(12) United States Patent
Sullivan et al.

(10) Patent No.: US 9,446,197 B2
(45) Date of Patent: Sep. 20, 2016

(54) INTRANASAL CARTRIDGE DEVICES

(71) Applicant: Mystic Pharmaceuticals, Inc., Cedar Park, TX (US)

(72) Inventors: Timothy R. Sullivan, Austin, TX (US); Jeffrey Nelson, Round Rock, TX (US)

(73) Assignee: Mystic Pharmaceuticals, Inc., Cedar Park, TX (US)

( * ) Notice: Subject to any disclaimer, the term of this patent is extended or adjusted under 35 U.S.C. 154(b) by 533 days.

(21) Appl. No.: 13/770,861

(22) Filed: Feb. 19, 2013

(65) Prior Publication Data

US 2013/0158474 A1   Jun. 20, 2013

Related U.S. Application Data

(62) Division of application No. 11/971,471, filed on Jan. 9, 2008, now Pat. No. 8,377,009.

(60) Provisional application No. 60/853,328, filed on Jan. 9, 2007, provisional application No. 60/944,700, filed on Jun. 18, 2007, provisional application No. 60/982,643, filed on Oct. 25, 2007.

(51) Int. Cl.
*A61M 5/30* (2006.01)
*A61M 11/06* (2006.01)
(Continued)

(52) U.S. Cl.
CPC .............. *A61M 5/30* (2013.01); *A61M 11/002* (2014.02); *A61M 11/007* (2014.02); *A61M 11/06* (2013.01);
(Continued)

(58) Field of Classification Search
CPC ........... A61M 5/145; A61M 5/14506; A61M 5/14533; A61M 5/2425; A61M 5/2448; A61M 5/2455; A61M 5/2459; A61M 5/28; A61M 5/282; A61M 5/283; A61M 11/007; A61M 11/06; A61M 15/0003; A61M 15/0028; A61M 15/0036; A61M 15/004; A61M 15/08; A61M 2205/073; A61M 2205/273; A61M 2205/276; A61M 2205/583; A61M 2205/284; A61M 2205/6081; A61M 2005/14533; A61M 15/007; A61M 15/06; A61M 2205/84; A61M 2205/60815

USPC .......... 604/68, 187, 200–206, 212–214, 218, 604/244, 275, 514, 520, 103, 162, 221, 322, 604/325, 326, 327, 386, 391, 541.4
See application file for complete search history.

(56) References Cited

U.S. PATENT DOCUMENTS

| | | |
|---|---|---|
| 1,870,558 A | 8/1932 | Darby |
| 2,105,946 A | 1/1938 | Lewis |

(Continued)

FOREIGN PATENT DOCUMENTS

| | | |
|---|---|---|
| EP | 1844809 A1 | 10/2007 |
| GB | 9125699 | 12/1991 |

(Continued)

OTHER PUBLICATIONS

Abelson, M.B. and Rosner, Sarah A., "Prevent Drugs From Going Missing in Action," Review of Opthalmology, Jun. 15, 2003, 10:6, pp. 96-98.

(Continued)

*Primary Examiner* — Bhisma Mehta
*Assistant Examiner* — Larry R Wilson
(74) *Attorney, Agent, or Firm* — Vinson & Elkins LLP

(57) ABSTRACT

Intranasal delivery devices include dosage forms containing medical compositions for use in the intranasal devices, and methods of delivering medical compositions to the nasal mucosa of users. The devices dispense a predetermined quantity of fluid into the nasal passage of a user, in which the predetermined quantity of fluid is contained in, or produced in a dosage form or blister that is crushed by a plunger with sufficient force to drive the dosage form against a piercing mechanism, piercing the dosage form and forcing the liquid contents from the dosage form and through a delivery channel into a spray to be directed into the nasal passage of a user. The plunger is connected to a trigger device by a linkage that confers a mechanical advantage to the trigger mechanism.

5 Claims, 35 Drawing Sheets

(51) Int. Cl.
*A61M 15/08* (2006.01)
*B05B 11/02* (2006.01)
*A61M 11/00* (2006.01)
*A61M 15/00* (2006.01)
*A61M 5/24* (2006.01)
*A61M 15/06* (2006.01)
*B05B 11/00* (2006.01)
*B05B 11/04* (2006.01)
*B05B 11/06* (2006.01)

(52) U.S. Cl.
CPC ....... *A61M 15/0003* (2014.02); *A61M 15/004* (2014.02); *A61M 15/0028* (2013.01); *A61M 15/0031* (2014.02); *A61M 15/0036* (2014.02); *A61M 15/0051* (2014.02); *A61M 15/08* (2013.01); *B05B 11/0081* (2013.01); *B05B 11/02* (2013.01); *A61M 5/2425* (2013.01); *A61M 15/06* (2013.01); *A61M 2202/0468* (2013.01); *A61M 2202/064* (2013.01); *A61M 2205/073* (2013.01); *A61M 2205/273* (2013.01); *A61M 2205/276* (2013.01); *A61M 2205/583* (2013.01); *A61M 2205/584* (2013.01); *A61M 2205/6081* (2013.01); *A61M 2206/16* (2013.01); *B05B 11/0035* (2013.01); *B05B 11/0083* (2013.01); *B05B 11/048* (2013.01); *B05B 11/062* (2013.01); *B05B 11/3056* (2013.01); *B05B 11/3057* (2013.01)

(56) References Cited

U.S. PATENT DOCUMENTS

| | | |
|---|---|---|
| 2,307,980 A | 1/1943 | Avrett |
| 2,332,799 A | 10/1943 | Hunn |
| 2,442,004 A | 5/1948 | Hayward-Butt |
| 2,706,984 A | 4/1955 | Lipari |
| 2,885,931 A | 4/1955 | McDonald |
| 3,507,277 A | 4/1970 | Altounyan et al. |
| 3,512,524 A | 5/1970 | Drewe |
| 3,888,263 A | 6/1975 | Watt et al. |
| 3,949,751 A | 4/1976 | Birch et al. |
| 3,971,377 A | 7/1976 | Damani |
| 4,013,075 A | 3/1977 | Cocozza |
| 4,017,007 A | 4/1977 | Riccio |
| 4,090,642 A | 5/1978 | Baker |
| 4,095,596 A | 6/1978 | Grayson |
| 4,105,027 A | 8/1978 | Lundquist |
| 4,116,195 A | 9/1978 | James |
| 4,206,758 A | 6/1980 | Hallworth et al. |
| 4,423,724 A | 1/1984 | Young |
| 4,623,337 A | 11/1986 | Maurice |
| 4,627,432 A | 12/1986 | Newell et al. |
| 4,798,288 A | 1/1989 | Holzner |
| 4,952,212 A | 8/1990 | Booth et al. |
| 4,966,581 A | 10/1990 | Landau |
| 5,152,284 A | 10/1992 | Valentini et al. |
| 5,154,710 A | 10/1992 | Williams |
| 5,207,217 A | 5/1993 | Cocozza et al. |
| 5,215,221 A | 6/1993 | Dirksing |
| 5,219,101 A | 6/1993 | Matkovich et al. |
| 5,273,190 A | 12/1993 | Lund |
| 5,287,850 A | 2/1994 | Haber et al. |
| 5,307,953 A | 5/1994 | Regan |
| 5,327,883 A | 7/1994 | Williams et al. |
| 5,337,740 A | 8/1994 | Armstrong et al. |
| 5,379,763 A | 1/1995 | Martin |
| 5,411,175 A | 5/1995 | Armstrong et al. |
| 5,425,480 A | 6/1995 | Rabenau et al. |
| 5,431,155 A | 7/1995 | Marelli |
| 5,433,343 A | 7/1995 | Meshberg |
| 5,469,989 A | 11/1995 | Graf et al. |
| 5,492,112 A | 2/1996 | Mecikalski et al. |
| 5,497,763 A | 3/1996 | Lloyd et al. |
| 5,524,419 A | 6/1996 | Shannon |
| 5,529,059 A | 6/1996 | Armstrong et al. |
| 5,547,131 A | 8/1996 | Brace |
| 5,683,361 A | 11/1997 | Elk et al. |
| 5,715,811 A | 2/1998 | Ohki et al. |
| 5,769,278 A | 6/1998 | Kummer et al. |
| 5,810,004 A | 9/1998 | Ohki et al. |
| 5,881,721 A | 3/1999 | Bunce et al. |
| 5,896,855 A | 4/1999 | Hobbs et al. |
| 5,901,703 A | 5/1999 | Ohki et al. |
| 5,921,236 A | 7/1999 | Ohki et al. |
| 5,924,417 A | 7/1999 | Braithwaite |
| 5,944,222 A | 8/1999 | Fuchs et al. |
| 5,950,619 A | 9/1999 | van der Linden et al. |
| 5,964,417 A | 10/1999 | Amann et al. |
| 5,970,974 A | 10/1999 | Van Der Linden et al. |
| 6,101,790 A | 8/2000 | Mori et al. |
| 6,105,761 A | 8/2000 | Peuker et al. |
| 6,109,479 A | 8/2000 | Ruckdeschel |
| 6,116,238 A | 9/2000 | Jackson et al. |
| 6,123,068 A | 9/2000 | Lloyd et al. |
| 6,135,755 A | 10/2000 | Zeiter et al. |
| 6,138,439 A | 10/2000 | McMahon et al. |
| RE37,047 E | 2/2001 | Py |
| 6,186,141 B1 | 2/2001 | Pike et al. |
| 6,321,942 B1 | 11/2001 | Krampen et al. |
| 6,367,473 B1 | 4/2002 | Kafer |
| 6,382,465 B1 | 5/2002 | Greiner-Perth |
| 6,425,888 B1 | 7/2002 | Embleton et al. |
| 6,443,152 B1 | 9/2002 | Lockhart et al. |
| 6,446,839 B1 | 9/2002 | Ritsche |
| 6,470,650 B1 | 10/2002 | Lohwasser |
| 6,484,715 B1 | 11/2002 | Ritsche et al. |
| 6,530,371 B2 | 3/2003 | Jansen et al. |
| 6,543,448 B1 | 4/2003 | Smith et al. |
| 6,644,309 B2 | 11/2003 | Casper et al. |
| 6,679,248 B2 | 1/2004 | Stadelhofer |
| 6,705,313 B2 | 3/2004 | Niccolai |
| 6,708,846 B1 | 3/2004 | Fuchs et al. |
| 6,725,857 B2 | 4/2004 | Ritsche |
| 6,726,665 B1 | 4/2004 | Embleton et al. |
| 6,730,066 B1 | 5/2004 | Bennwik et al. |
| 6,732,732 B2 | 5/2004 | Edwards et al. |
| 6,758,837 B2 | 7/2004 | Peclat et al. |
| 6,772,915 B2 | 8/2004 | Helmlinger |
| 6,782,887 B2 | 8/2004 | Sullivan |
| 6,877,672 B2 | 4/2005 | Stihl |
| 6,889,690 B2 | 5/2005 | Crowder et al. |
| 6,929,005 B2 | 8/2005 | Sullivan et al. |
| 6,957,909 B1 | 10/2005 | Dingeldein et al. |
| 7,097,075 B2 | 8/2006 | Peuker et al. |
| 7,143,765 B2 | 12/2006 | Asking et al. |
| 7,669,597 B2 | 3/2010 | Sullivan et al. |
| 7,963,089 B2 | 6/2011 | Nelson et al. |
| 8,047,204 B2 | 11/2011 | Sullivan et al. |
| 2003/0199832 A1 | 10/2003 | Greiner-Perth et al. |
| 2004/0163645 A1 | 8/2004 | Connelly et al. |
| 2005/0000518 A1 | 1/2005 | Dunkley et al. |
| 2005/0016533 A1 | 1/2005 | Schuler et al. |
| 2005/0022813 A1 | 2/2005 | Alston |
| 2005/0048003 A1 | 3/2005 | Ohki et al. |
| 2005/0051166 A1 | 3/2005 | Glusker et al. |
| 2005/0056280 A1 | 3/2005 | Alston et al. |
| 2005/0081852 A1 | 4/2005 | Rangachari |
| 2005/0119605 A1 | 6/2005 | Sohn |
| 2005/0150492 A1 | 7/2005 | Dunkley et al. |
| 2005/0238708 A1 | 10/2005 | Jones et al. |
| 2006/0147389 A1 | 7/2006 | Staniforth et al. |
| 2006/0237009 A1 | 10/2006 | Jones et al. |
| 2007/0051362 A1* | 3/2007 | Sullivan .............. A61M 31/00 128/200.23 |
| 2008/0123465 A1 | 5/2008 | Heusser et al. |
| 2008/0177246 A1 | 7/2008 | Sullivan et al. |
| 2008/0283439 A1 | 11/2008 | Sullivan et al. |
| 2010/0331765 A1 | 12/2010 | Sullivan et al. |

(56) References Cited

U.S. PATENT DOCUMENTS

2011/0247305 A1   10/2011   Nelson
2011/0277763 A1   11/2011   Sullivan et al.

FOREIGN PATENT DOCUMENTS

| WO | WO94/20408 | 9/1994 | |
|----|------------|--------|---|
| WO | 9600050 | 1/1996 | |
| WO | 9723177 | 7/1997 | |
| WO | WO 2005032998 A1 * | 4/2005 | ......... B05B 11/3056 |
| WO | 2005102058 A2 | 11/2005 | |
| WO | WO2005/102058 | 11/2005 | |
| WO | WO2008/086413 | 7/2008 | |
| WO | WO2008/144439 | 11/2008 | |
| WO | WO2009/036422 | 3/2009 | |

OTHER PUBLICATIONS

Abelson, M.B. and Shapiro, A., "Hitting the Bull's-eye With Drug Delivery," Review of Opthalmology, Jul. 15, 2003, 10:7, pp. 82-84.

Aurora, Jack, "Nasal Delivery, Articles: Development of Nasal Delivery System: A review," Drug Delivery Technology, 2002, 2(7); pp. 70-73.

Lofgren, Anders et al., "Blow-Fill-Seal Pharmaceutical Packaging—Towards Safe and Convenient Medical Containers" Business Briefing: Pharma Outsourcing, Jan. 2004, pp. 78-81.

Jenevieve B. Polin, "Blow-Fill-Seal Technology for Unit Dosing," Pharmaceutical & Medical Packaging News, Sep. 2003.

O'Riordan, Thomas G., "Inhaled Antimicrobial Therapy: From Cystic Fibrosis to the Flu," Respiratory Care, Jul. 2000, vol. 45, No. 7, pp. 836-845.

Saettone, Marco F "Progress and Problems in Opthalmic Drug Delivery," Business Briefing: Pharmatech, May 2003, pp. 167-171.

Salt, Alec N., "Simulation of Methods for Drug Delivery to the Cochlear Fluids," Felix D. Oestreicher, e. (eds.): Rational Pharmacotherapy of the Inner Ear. Adv. Otorhinolaryngol. Basel, Karger, 2002, vol. 59, p. 140.

Guidance for Industry, "Container Closure Systems for Packaging Human Drugs and Biologies," U.S. Dept. of Health and Human Services, FDA, CDER, CBER, May 1999.

Guidance for Industry, "Sterile Drug Products Produced by Aseptic Processing—Current Good Manufacturing Practice," U.S. Dept. of Health and Human Services. FDA, CDER, CBER, ORA, Sep. 2004.

* cited by examiner

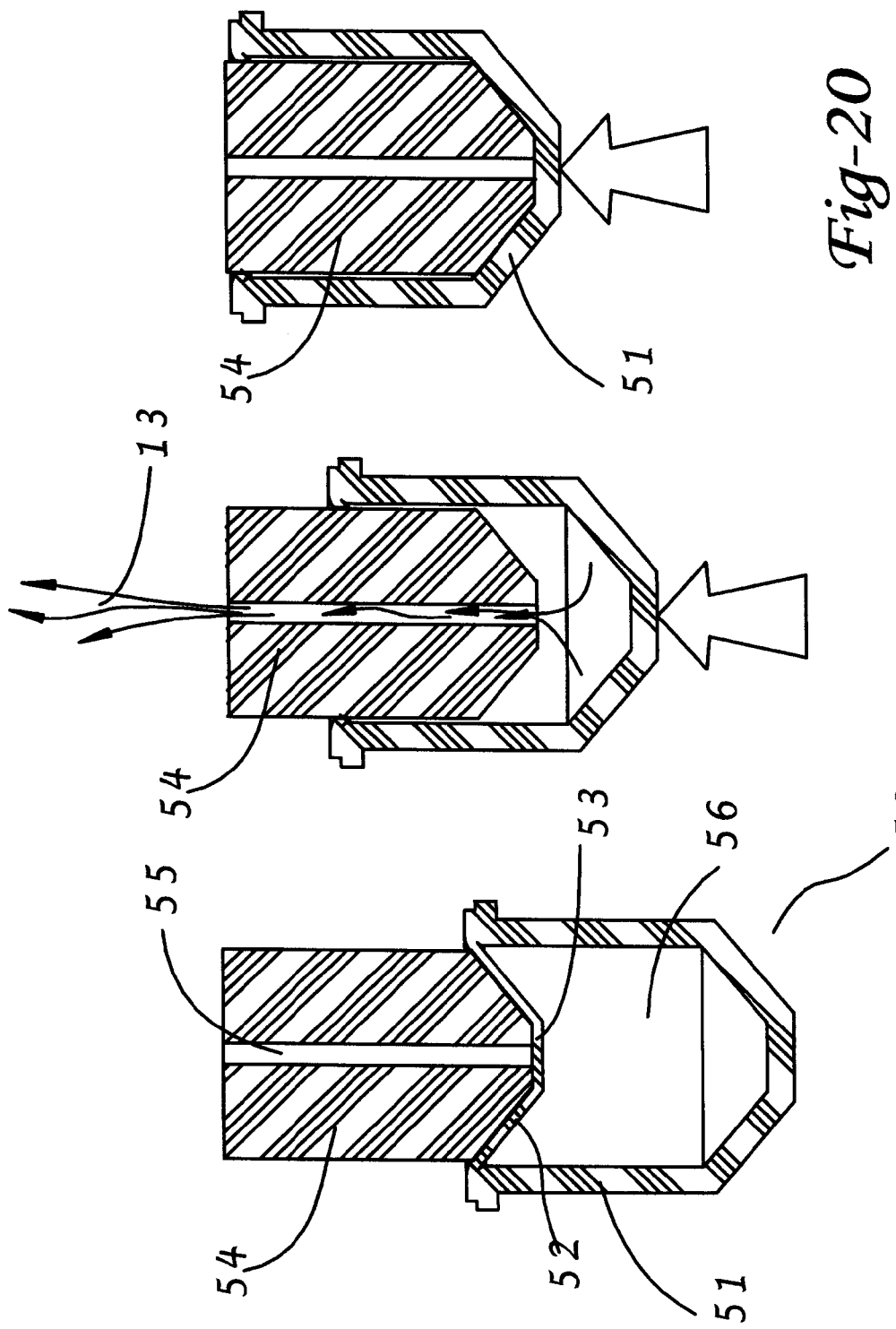

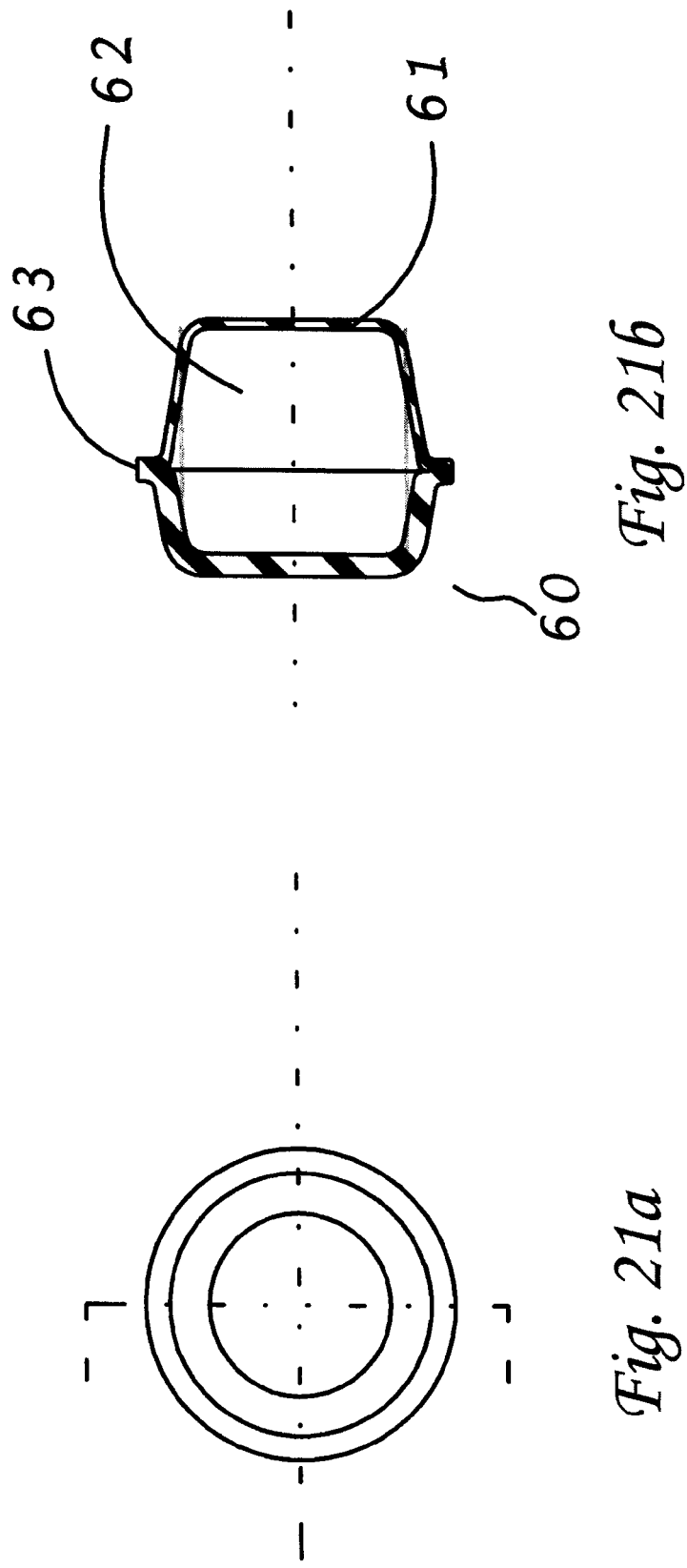

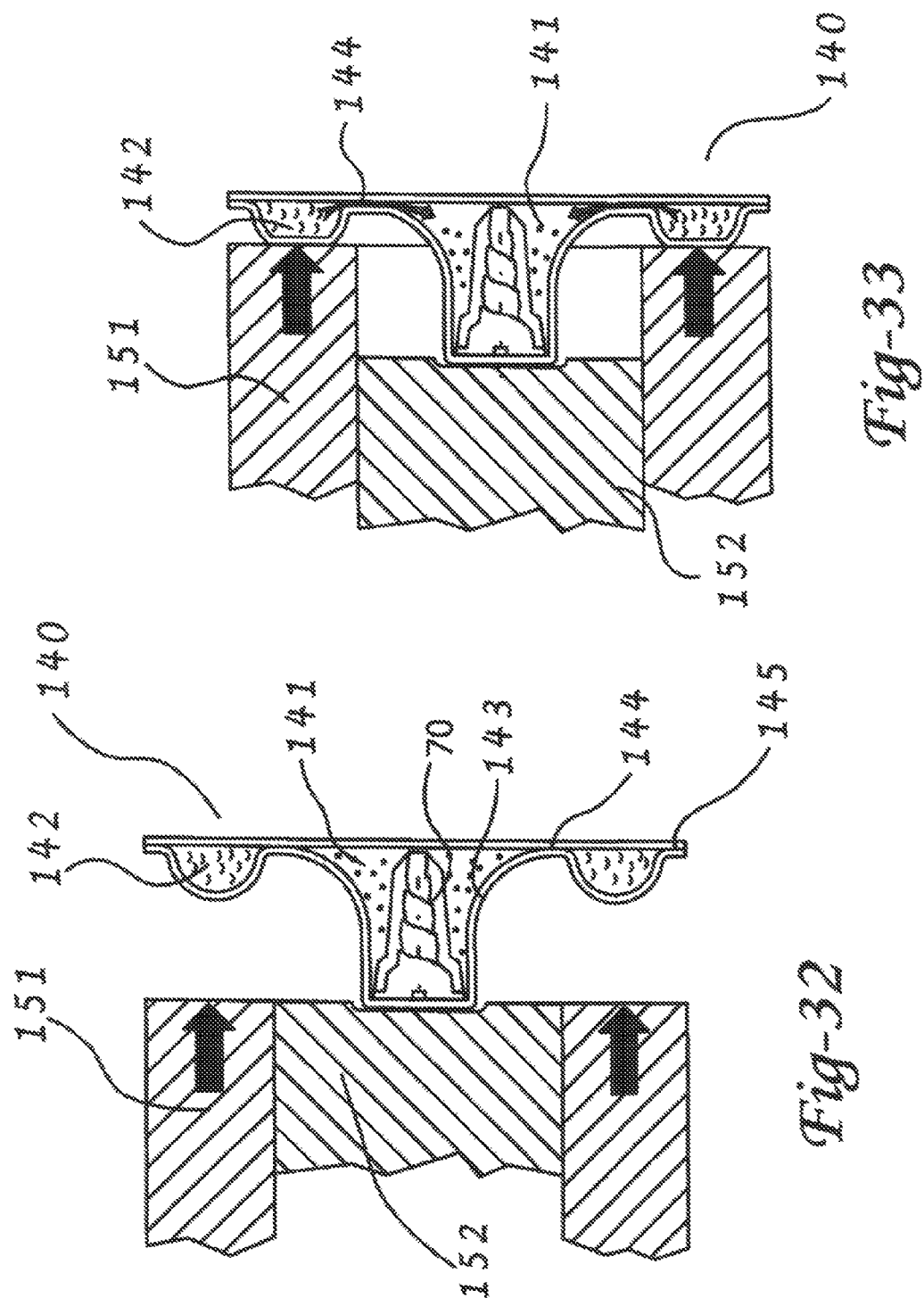

INTRANASAL CARTRIDGE DEVICES

CROSS-REFERENCE TO RELATED APPLICATIONS

This application is a divisional of U.S. Ser. No. 11/971,471, filed Jan. 9, 2008, and claiming benefit of priority of U.S. Provisional Application Ser. No. 60/853,328, filed Jan. 9, 2007, U.S. Provisional Application Ser. No. 60/944,700, filed Jun. 18, 2007, and U.S. Provisional Application Ser. No. 60/982,643, filed Oct. 25, 2007, the disclosures of all of which are incorporated into this application in their entirety by reference for all purposes. In addition, the disclosures of commonly owned U.S. Provisional Applications Ser. No. 60/938,379, filed May 16, 2007 and 60/978,619, filed Oct. 9, 2007 are also incorporated into this application in their entirety by reference for all purposes.

STATEMENT REGARDING FEDERALLY SPONSORED RESEARCH OR DEVELOPMENT

N/A

BACKGROUND OF THE INVENTION

There is a growing number of drugs and vaccines for which the most effective, or most convenient method of administration is by intranasal delivery. This has led to the development of dosing devices for spray into the nose. These devices must deliver a precise dosage amount and it is important to deliver the dose in a way that the drug is absorbed in the nasal cavity and does not enter the back of the throat or the lungs.

Another issue that arises with intranasal drug delivery devices is the potential for abuse. Many drugs with a substantial potential for abuse are sprayed or snorted into the nose by drug abusers. One aspect of intranasal device design, therefore, is to prevent the re-use or re-tasking of a used drug intranasal device. A powder dispenser device described in U.S. Pat. No. 5,683,361 provides a chamber with a powdery drug in which the chamber has a penetrable membrane enclosing either end. To dispense the drug, a plunger and piston are pressed against the lower end of the drug chamber, forcing it against a penetrating device connected to the dispensing nozzle and thus breaking the upper membrane. As the piston is depressed further, the lower membrane is penetrated by a lower penetration device, thus allowing the pressurized air above the piston to enter the drug chamber and expel the drug through the nozzle. This device requires that the air above the piston must be sterilized as well as the drug containing chamber, thus requiring sterilization of the entire device and secondary packaging. Another single dose dispenser is described in U.S. Pat. No. 5,307,953. This device also includes a plunger and a sealed drug containing chamber. A stainless steel needle is provided that communicates with the outlet nozzle. As the plunger is pressed by a user, the drug chamber is forced against the needle, which penetrates a membrane that seals the drug chamber. As the piston is pressed further, the drug is forced through the needle and out the nozzle.

U.S. Pat. No. 5,944,222 describes a dosing device in which a piston forces a drug containing chamber against a needle for release through the nozzle. The described device also includes a material bridge between the piston and the casing. By examining this bridge, one can determine if the piston has been previously pressed into the cylinder. This makes a tamper-evident closure so that it is apparent when someone is attempting to re-use a spent device.

A similar device with a piston and penetrating needle is described in U.S. Pat. No. 6,708,846. This device can also be placed in a reusable activating unit. The unit includes a ram which is adjustable with threads on the ram and on a sleeve containing the ram. During use of this device, a dispensing device is placed in the actuating unit and the ram is threaded into the sleeve so that the head of the ram rests against the piston of the dispensing device. A release detent holds the ram in place and prevents unwanted penetration of the drug compartment. The ram is also pressed against a compressed spring. Pressing the release button releases the detent, allowing the ram to push the piston and discharge the drug. A knob is then turned to reset the actuating device so it can receive another dispensing device for reuse.

Another dispenser, described in U.S. Pat. No. 6,725,857 is designed to dispense multiple doses of a drug, and is also designed for one-handed operation. Multiple drug doses are contained in storage chambers on a blister strip in the form of a drum store so that the strip is contained in the body of the device and is moved along a wheel as each dose is dispensed. An actuating lever is pressed against a spring and when the spring is compressed, a lock holding a carrier plate is released. The compressed spring then drives the plate and attached slides that push the wheel so that the next dose chamber is aligned with the punch, the punch is moved down into the chamber, puncturing the enclosing film, and air pressure created within the body of the device expels the drug from the chamber. The user then returns the actuating lever to the original position and the process can be repeated for the next dose.

SUMMARY

The present disclosure provides drug or pharmaceutical delivery devices, unit dosage forms containing medical compositions for use in the devices, and methods of delivering medical compositions to a user. As used herein, the term "unit dosage form" is intended to convey its art accepted meaning, and includes, but is not limited to ampul (ampoule), blister, cartridge, bottle, vial, unit-dose vial, or container, which terms are used interchangeably herein. In preferred embodiments, an unit dosage form contains a single-unit dose of a substance, or a two-unit dose of one substance or two different substances, in one or more compartments of the unit dosage form. Alternatively, an unit dosage form may administer three or more substances from one or more compartments in an unit dosage form. During manufacture, the unit dosage forms can be singulated, i.e., individually broken apart and individually loaded into, for example, an unit dosage form cartridge or a device. Alternatively, the unit dosage forms can be interconnected, for example through a strip, disk or connected webbing. The unit dosage forms can be manufactured as a disk or strip of unit dosage forms, which then may be manipulated into different forms for administration, such as a circle, ring, or tube. In other preferred embodiments, the unit dosage forms themselves, or the Unit dosage form Cartridge Holder, adhere to a numbering, color coding, icon system coding, or Braille system for assisting the user in administration of the unit dosage forms, and may also include a bar code or Radio Frequency Identification Device (RFID).

In certain embodiments the unit dosage forms of the present disclosure are blisters that can be manufactured as described in U.S. Provisional Ser. No. 60/972,634, incorporated in its entirety herein by reference. The manufacturing processes for shaping articles for unit-dose packaging with at least one formed recess (e.g., a blister), in particular for unit-dose packaging of pharmaceutical dosage forms, can include a step of drawing the film material (e.g., metal-plastic foil) with one or more plungers to form a primary contour, the contour having a depth of at least 100% and up to 150% of the depth of the formed recess. A second stage involves shaping the primary contour with one or more plunger(s) to the desired formed recess, with a depth that is less than the depth of the primary contour, while substantially maintaining the surface area of the primary contour formed in the first stage. The formed recess may be formed using warm-forming or cold-forming techniques.

The disclosed devices may be described in certain embodiments as devices for dispensing a predetermined quantity of fluid into the nasal passage of a user, or into the eye or ear of a user, in which the predetermined quantity of fluid is contained in, or produced in an ampul or blister dosage form that is crushed by a plunger with sufficient force to drive the dosage form against a piercing mechanism, piercing the dosage form and forcing the liquid contents from the dosage form and through a delivery channel into a spray to be directed to the user. A predetermined quantity refers, in most instances to a single dose of medication or a pharmaceutical or medical composition, and in certain embodiments to a prescribed dose. A predetermined quantity of fluid may also be a partial dose when delivery of a dose is administered in two or more spray events. Any pharmaceutical agent that is deliverable in a powder or liquid from is contemplated in the present disclosure, including but not limited to antibiotics, antipyretics, anti-inflammatories, biologics, vitamins, co-factors, enzymes, inhibitors, activators, nutrients, aptamers, thioaptamers, vaccines including killed or live virus or microorganisms, nucleic acids, proteins, peptides, antibodies, peptide mimetics, or other agents known in the art. The medical compositions are in the form of a liquid, a powder, or a combination of liquid and powder and include one or more active agents and combinations of pharmaceutically acceptable carriers, solvents, diluents, preservatives, surfactants, salts, adjuvants, viscosity agents, buffers, chelators, or other ingredients known to those in the art as needed.

Although preferred embodiments of the devices are described herein primarily for use as intranasal delivery devices, it is understood that in certain embodiments the described devices can also be used for delivery to the eye, ear, mouth, lungs, or topical cutaneous areas of a user, by modification of the nozzle end of the devices. The devices can also be produced for veterinary use, for delivery of drugs to the nose, eye or ear of an animal. For example, a device may include a nozzle for delivery into the ear canal of a user, or it may include a cup or nozzle for delivery to the eye of a user. The volume of a dose delivered for the various uses can also be adjusted as appropriate.

The volume of droplets or particles dispensed from the devices will depend on the site of dispensing as well as the content and viscosity of the medication to be delivered. In certain embodiments droplet to be delivered to the eye would be from 1 µl to 25 µl, or more typically from 7 µl to 25 µl. Dosage for nasal administration are typically from 75 µl to 500 µl and dosages for oral or topical cutaneous administration can be larger, as much as 1000 µl or more. The volume and size of droplets or particles released by a device can be adjusted to maximize the therapeutic benefit of the dispersed substance. The volume of substance dispensed depends on the size of the compartment containing the substance, the unit dosage form blister, the piercer, the fill level, the degree to which the dosage form is compressed by the device and other variables in the construction of the devices, as well as characteristics of the substance dispersed, which are well understood by those skilled in the art. These variables can be appropriately dimensioned to achieve dispersal of a desired volume or droplet size of liquid or particle size of substance to the user. One of skill in the art understands that residual liquid or other substance after dispersal is taken into account when formulating the appropriate parameters for dispersing the desired dosage volume.

An advantage of the devices and unit dosage form designs set forth herein is that the sterility of the administered substance is maintained until the moment of use. Maintaining sterility until the moment of use minimizes or eliminates the need to use preservatives or bacteriostatic compounds in the substances administered, without risking contamination. In addition, if the unit dosage form is damaged, or is otherwise defective, the devices do not administer the substance, which may no longer be sterile. For example, if an unit dosage form is defective in the area of the pierceable section, or develops a leak, the devices will not dispense the substance properly because sufficient pressure will not be generated in the unit dosage form to effectively release the substance.

The devices typically include a body with a nozzle end for insertion into the nostril of a user, a trigger device to be operated by a user, a dosage form, either an ampul or a blister, containing a composition to be delivered and including a piercable membrane, a cavity within the body or nozzle containing the dosage form, a plunger or piston body, an actuator mechanism linking the trigger device to the plunger, a piercing mechanism positioned to pierce the dosage form upon activation of the trigger, and a discharge channel to release a spray of the liquid composition through the nozzle in a predetermined spray plume geometry and direction.

The dosage forms of the disclosure are described, in certain embodiments as including a dispensing blister chamber that contain a piercing device, wherein the piercing device is a substantially hollow, elongate member with a base end and a piercing tip opposite the base end and providing a discharge nozzle. In certain embodiments the dispensing blister conforms to at least the base end of the piercing device effective to support and hold the piercing device in place during manufacture and use of the dosage form. The piercing devices include one or more inlet openings on or near the base end and an internal conduit providing fluid communication between the one or more inlet ports and the discharge nozzle; and the surface of the internal conduit comprises structural features such as contours, steps, flutes, ribs, constrictions, or a combination thereof to control the spray pattern and droplet size of a fluid forced through the piercing device. It is a further aspect of the disclosure that the inlet openings provide a fluid path from the interior of the dispensing blister chamber into the internal conduit that comprises one or more bends, and that the combination of angular turns and the structural features of the internal conduit create vortices in the fluid as it is forced through the piercing mechanism.

The structural features can be designed, for example, for different types of spiral, vertical and other flow and the design can be adjusted for different viscosities of the fluid or solid to be dispensed. For example, structural features may be added to create a vortex, to further mix the contents of the blister, to change the fluid property type from laminar to turbulent or vice versa or to change fluid properties such as pressure, velocity, surface tension or viscosity. Additionally, the inlets into the internal conduit can include bends of angles from about 0° to 90°, or more combinations in order to create the desired spray plume geometry for a particular medicament or liquid dose.

In certain embodiments, a shaped blister dosage form as described herein that contains medication and an internal piercing nozzle, is configured for use in a smaller diameter dispensing mechanism, while still providing an accurate dose of medicine in the form of a controlled spray. A blister strip including a plurality of such dosage forms can include a blister material layer in which the dosage forms are formed, and a lid material bonded to the blister material. A concentric sealing area provides a resilient seal that is not broken when the dosage forms are crushed to deliver the contained medication.

To produce a controlled spray of liquid when bursting a sealed formed recess, such as a shaped blister, an internal piercer inside the sealed blister may be used, and may be positioned such that it maintains contact with the lid material. Internal piercers are disclosed in U.S. Ser. No. 11/114,251, U.S. Prov. Nos. 60/853,328 and 60/944,379, each of which is incorporated herein by reference. The internal piercer can take different shapes, including but not limited to a funnel design, or a disc shape design. The internal piercer can constructed of materials any suitable materials such as ceramic, glass, metal, styrene, polystyrene, plastics, including but not limited to PET, polypropylene, polyethylene, or PEEK, and other pharmaceutical grade FDA approved materials of sufficient hardness to penetrate the lid material. The second, subsequent and/or final plunger(s) may be designed to shape the formed recess such that the internal piercer is locked into place within the formed recess, e.g., through manufacture, handling, transportation, storage, and actual use. For example, in a shaped blister, a protruding structure, an indentation, a diaphragm or an annulus is formed to conform to the shape of the base of the internal piercer. The protruding structure, indentation, diaphragm, or annulus provides support for and holds the internal piercer in place during assembly and during dispensing. Thus, these structures functions to capture the internal piercer (e.g., restrict vertical movement of the piercer), thereby holding it in place. The internal piercer may also be held in place through manufacture and actual use by, for example, press fit, welding, hydrostatic forces, or electrostatic forces. The shaped blister can also be formed by the second or subsequent plunger such that it insures that the protruding structure, indentation, diaphragm, or annulus seals to the internal piercer in order to achieve the desired spray pattern.

In preferred embodiments, the internal piercer includes a hollow tube or channel (the delivery channel) through which the pharmaceutical dosage form flows as the shaped recess is compressed and pierced. The tip of the piercer preferably has an angled edge to aid in penetration of the lid material. The inside diameter of the piercer tube can range from about 0.015 inches to about 0.05 inches, but in certain preferred embodiments is about 0.025 inches. The internal diameter, shape, or surface texture of the delivery channel, whether in, near, and/or at the exit point, may contain a nozzle or may be varied to form the optimum droplet size and spray plume geometry of the pharmaceutical dosage form as it exits the shaped article, as well as control the velocity, pressure, pattern, distribution, and aim of the released substance. Thus, the nozzle system and the piercer may be integrated into a single unit. The nozzle system can also be designed to determine the mixing of the substance as it is released.

To successfully dispense the medication, the medication must flow through the piercing nozzle with enough velocity to create the desired spray geometry. As described herein, this is accomplished by pressing on the blister form with sufficient force to push the piercing nozzle through the lid material, completely crushing the dosage form and forcing the contents through the nozzle with the required velocity. During this dispensing operation, the seal of the lid material to the blister material must be strong enough that no leakage occurs prior to the nozzle piercing the lid. The smaller size required by certain dosage situations, such as intranasal administration present greater challenges to the seal of the lid material to the blister material.

It is an aspect of the disclosure that the disclosed devices also include actuator mechanisms that provide a mechanical advantage, a mechanical disadvantage, or a combination thereof to the discharge process. Mechanical advantage, as used herein, indicates that the amount of force exerted on the plunger or piston to crush a dosage form and deliver the medication is greater than the amount of force applied by a user on the trigger device. Mechanical disadvantage, as used herein, indicates that the amount of force exerted on the plunger or piston is less than the amount of force applied by a user on the trigger device. In certain embodiments, the actuator mechanism provides a mechanical disadvantage during a first stage of the firing action and a mechanical advantage during a second stage of the firing action. In an example of such a system, an actuator can provide a mechanical disadvantage in a first stage of the firing process, forcing a user to exert an increased level of force to the trigger mechanism, during the firing process, the actuator can then shift to a mechanical advantage in which the increased force being exerted by the user is enhanced to provide sufficient force to correctly dispense the dosage. It is understood that the first and second stages, however, do not necessarily refer to the time position in the firing order, but could occur in reverse order. The devices are thus able to drive the plunger with sufficient force to crush the dosage form and deliver the composition in the dosage form through the nozzle with sufficient force to create the desired spray pattern and geometry.

In certain embodiments, the mechanical advantage is provided by a toggle mechanism. The toggles of the present disclosure include jointed rods or bars with several flex points so the toggle is joined to the trigger device by a flexible joint and joined to the piston device with a flexible joint. The toggle further includes a flex point at or near the center of the bar or rod. At the flex point, the two sections of the toggle form at an angle of about 90° or greater. It is understood that at 90°, the force at the apex and at the end of the linkage are in a 1:1 ratio, but as the angle increases, the force at the piston end becomes greater than the force at the apex. As such, the angle formed at the apex may any angle that is about 90° or more, including 90°, 95°, 100°, or even 135° to provide the required amount of mechanical advantage. The apex of this angle contacts the trigger device when the device is in the ready mode or position. When the trigger is then activated or pressed by a user in the direction of the angle bisector, as the toggle moves away from the direction of force and the plunger is pushed against the dosage form flattening the angle in the toggle toward 180°, then the force applied to the end of the toggle that is joined to the plunger is greater than the force applied at the apex of the angle.

Certain disclosed devices include an activation knob that is rotatable from an inactive to an active position. The activation knob is particularly suitable for use with a toggle mechanism for providing mechanical advantage. In the inactive or storage position the knob, the cross section of the knob conforms to the shape of the body of the device such that the long axis of the knob is aligned with the long axis of the body. The knob is joined to the toggle is such a way that the plane of the angle in the toggle is also aligned or parallel to the long axis of the body. Rotating the knob through 90° into the ready position, places the long axis of the knob perpendicular to the long axis of the body, and raises the angled toggle against the button or trigger device. This pushes the button up into the ready, or cocked position. In certain embodiments, the underside of the button provides a depression that complements the geometry of the toggle and prevents the toggle from slipping when the button is pushed.

The described devices include devices designed for a single use, or the devices are designed to be disposable after a single use. Certain devices are also reloadable or capable of holding and/or dispensing more than a single dose. The devices incorporate designs that prevent a reuse of or repurposing of the devices. The toggle can be made of an inexpensive material, therefore, such as a semi-rigid plastic or polymer material, or of any other semi-rigid material known in the art including metals such as aluminum, for example. The toggle mechanism can be made of a single piece of material in which the activation knob, actuator and plunger are all formed of a single piece, or the mechanism can be made of two or more pieces. The toggle can be made of two bars, joined at the center with a hinge pin, and joined at either or both ends with hinge pins or other flexible joints.

In certain embodiments the mechanical advantage of the actuator can be provided by a pivoting linkage. A device with a pivot mechanism can include a pivot arm and a grip arm designed so a user holds the device in one hand with the fingers on the pivot arm and the thumb on the grip arm. The device is fired by squeezing the fingers and thumb together to bring the pivot arm into contact with the grip arm, or the progress of the pivot arm toward the grip arm can be limited before it reaches the grip arm, by the length of the piston stroke. The pivot arm includes an attachment to the body at a pivot point and a projection that enters the body of the device, forming a pivot ram that contacts the plunger or piston body. The pivot ram is closer to the pivot point than to the opposite end of the pivot arm. This placement of the pivot ram provides the mechanical advantage to the pivot mechanism.

An aspect of the design of a pivot arm device is the placement of the device during use. In order to deliver the full dosage amount to a user when the device is for intranasal delivery, it is important that the pharmaceutical is delivered and absorbed to the nasal mucosa rather than entering the throat or lungs of the user. The pivot device is designed to provide the correct alignment. When the device is held in the hand of a user as described and the discharge nozzle is placed into a nostril of the user, placing the thumb in the depression in the chin under the lower lip provides for the correct alignment. This method of holding the device also provides stability so the device can be held steady when the user fires it.

In certain embodiments, the mechanical advantage can be provided by a lever mechanism. In preferred embodiments the lever mechanism includes a lever arm in which the linkage is connected to the lever arm by a slidable hinge and pin connection. In this embodiment, a pin near the end of the linkage member or actuator slides in a groove or slot in a hinge attached to the lever arm. In the storage position, the lever arm is folded against the body, and as the arm is raised to the ready position the linkage slides in the slot until the end of the mechanism comes to rest in a notch in the underside of the lever arm. Placement of the end of the linkage in the notch prevents the linkage from sliding back along the lever arm and provides a steady base from which to force the linkage against the plunger. The mechanical advantage is provided by the placement of the notch nearer the attachment point of the lever arm to the body than to the end of the lever arm. Certain devices can include an alignment device to correctly position the device for delivery to the nasal mucosa. A bite arm is extendable from the body, in a position such that when the discharge nozzle is placed in a nostril of a user and the bite arm is held in the teeth of the user, the device is positioned to control the direction of the discharge into the nasal passage of a user during use.

The mechanical advantage of the delivery devices disclosed herein can also be provided by one or more inclined planes. In these embodiments, typically a button projects from the rear of the device, or the side furthest from the discharge nozzle. The button is connected to an actuator that is an elongated member with a wedge-shaped projection toward the top of the device. This wedge shaped projection acts as an angled cam. The end of the linkage opposite the button is a ram for contacting and crushing a dosage form such as an ampul or blister. In such an embodiment, the angle of the camming surface or surfaces can be designed to provide a mechanical advantage, a mechanical disadvantage or a combination by a change in the slope or angle of the cam surface. The button, linkage or actuator and ram are rigidly connected and can be constructed of a single piece of a hard plastic or metal material. In this mechanism, the firing button, disposed on the top of the device also includes a projection, which may be an elongated member, a square or rectangular projection or an or angled cam or plane, projecting downward from its lower or inside surface. As the activation button is pushed in, the forward face on the linkage cam moves in a forward direction, contacting the projection on the cam on the firing button, thus raising the firing button into the ready position, and positioning the ram adjacent an ampul or blister. In the ready position, the firing button projection contacts the opposite face of the cam such that pushing the firing button down forces the linkage forward into the ampul, and providing a mechanical advantage relative to the force applied to the button. In certain embodiments the two faces of the actuator cam are formed by a single wedge-shaped structure, or they may be separate structures.

The disclosed devices can also provide a mechanical advantage or disadvantage to the firing process through the use of a spring or electro-mechanical mechanism. Examples of such mechanisms are described in commonly owned U.S. application Ser. No. 11/114,251, incorporated herein in its entirety by reference.

In certain embodiments, an inclined plane or angled cam mechanism is used in devices designed to deliver two or more sequential dosages. An example of such a device is an elongated tube-like device with a delivery nozzle at each end. The linkage is a sliding member with a ram at either end and one or more angled cam projections configured to interact with one or more angled cams projecting from a firing button. The sliding mechanism can be moved toward either end of the device to place the ram and button in ready position for firing a dose from the selected end. After a first dosage is dispensed, the sliding member can be moved to the opposite in ready position and then fired to dispense a second dose from that end.

It is a further aspect of the disclosure that the described devices can include a latch that locks the dispensing mechanism upon discharge, thus preventing re-use or re-purposing of the device. In certain embodiments a hook-shaped latch is forced into a similar opposite facing hook-shaped latch when the devices are fired, locking the pieces together and preventing reversal of the process to return the device to ready position. The latches may be on the actuators or on the pistons and mate with similar latches on the body of the devices. In certain embodiments, the linkage device is designed to break or separate when the plunger has reached its full stroke, thus disabling the device for further use. As a further safety feature, the devices can be designed such that the bodies cannot be opened without destroying the device to prevent re-use.

In certain embodiments the devices also include detent devices. A detent can be a projection, tab or flange on the plunger or piston, for example, that impinges on a groove or slot in the body. The detent is semi-rigid so that it resists a certain amount of force, and only flexes and thus releases the piston when a sufficient, predetermined force is applied. In this way, the devices ensure that sufficient force is applied to the piston to completely crush the dosage form and deliver the entire dose in the desired spray geometry.

The devices of the present disclosure can employ a piercing mechanism that is external to the dosage form, or they may employ dosage forms that contain an internal piercing mechanism. Preferred piercing mechanisms include a piercing point positioned adjacent the piercable membrane of the dosage form and a tube providing fluid communication from the piercing point to the discharge nozzle. In certain embodiments the piercing mechanism comprises a piercing body, wherein the outer dimensions of the piercing body closely fit in the inner dimensions of the dosage form such that when the piercing body pierces the dosage form and discharges the fluid during use, the piercing body displaces substantially the entire internal volume of the dosage form.

In certain embodiments the piercing mechanism is contained in the dosage form with the fluid to be delivered. Such internal piercing mechanisms can include an internal chamber, one or more inlet openings arranged to force one or more bends or changes in direction as the fluid flows into the internal chamber, a discharge outlet, and features on the internal surface to control the spray pattern and droplet size of a fluid forced to flow through the nozzle. The changes in direction can be of any appropriate angle, including from about 1° to about 90° or more. The design of such features are known to those of skill and include steps, flutes, ribs, or a combination thereof.

Certain embodiments of the delivery devices of the disclosure can be reusable. A reusable device can include a removable tip that contains one or more dosage forms and a piercing mechanism. The dosage form can be swaged into the removable tip thereby reducing the overall diameter of the dosage form while preserving the seal area of the dosage form. The piercing mechanism can be contained in an internally pierced dosage form as described herein. The removable tip is fit onto the body to place the dosage form adjacent the plunger, and can be connected to the body with a bayonet fitting, or other type of connection known to those of skill in the art.

The present devices can also be designed to provide the dosage in two separate discharges. Such devices can include a rotatable tip, for example that controls the amount to be discharged. The tip is designed so a shoulder in the interior of the tip is contacted by a tab on the plunger, stopping the plunger and thus the discharge when the dosage form is partially emptied. In certain embodiments the plunger stops when the dosage form is half empty. Rotating the tip, then, would rotate the shoulder away from the tab, aligning a channel or multiple channels with one or more tabs on the plunger. This second alignment would allow the rest of the dose to be dispensed when the trigger is again activated. In preferred embodiments the tip includes position indicators and the body includes an alignment mark. In this way, when a "1" on the tip is aligned with the alignment mark on the body, the device will dispense the first portion, and when a "2" is aligned with the alignment mark the device will dispense the remaining dose. Any numbers, letters, symbols, colors or other indicators can be used on the tip to indicate the position of the tip for dispensing drug. It is also understood that there can be a position marked "0" for example, in which the device is locked and cannot be used until the tip is rotated to the first active position. In this embodiment, a series of detent mechanisms may be used so that the detent is active for each portion of the dose.

In certain embodiments the disclosure may be described as a piercing nozzle for dispensing fluid from a dosage form in a controlled spray pattern and droplet size. The nozzle includes a substantially elongate member with an inlet end and a discharge end, an internal channel connecting the inlet end and the discharge end in fluid communication, one or more inlet openings in the inlet end, a discharge opening in the discharge end, and features on the internal chamber surface to control the spray pattern and droplet size of a fluid forced through the nozzle. The inlet ports are designed to provide a fluid path into the internal channel that includes one or more right angle turns. The inlet ports can also be designed to produce a vortex in the liquid as it is forced through the ports. Features in the internal channel can also include, but are not limited to steps, flutes, ribs, and related structures to produce the desired droplet size and spray geometry. In certain embodiments, the piercing tip may be on the discharge end of the elongated member, or on the inlet end. The piercing nozzle can be contained in a dosage form. The disclosure includes, therefore, a dosage form containing the piercing nozzle and a medical or pharmaceutical composition.

In certain embodiments the present disclosure can be described as an internally pierced dosage form that includes a substantially dome shaped, flexible blister, a substantially round pierceable surface sealed to the base of the dome-shaped blister, and an internal chamber containing a piercing nozzle as described herein and a liquid composition. In certain embodiments the piercing nozzle includes a base and a piercing end, and wherein the base is attached to the dome shaped blister and the piercing end is proximate the piercable surface.

Certain embodiments of the disclosure include dosage forms in which two or more components are mixed just prior to dispensing. Such a dosage form can include a blister and a backing, where the blister is divided into two or more chambers. The chambers are divided by seals that are less adhesive than the primary seal that surrounds the circumference of the total blister. In this embodiment, each chamber contains a powder or liquid portion of the final dose to be mixed, and at least one chamber contains a liquid such that the final mixture is in liquid form. It is an aspect of this embodiment that the contents of one chamber is forced into the interior of an adjacent chamber where the two components are mixed. This is accomplished by applying a force to the first chamber that is sufficient to break the less adhesive seal between chambers without breaking the primary circumferential seal around the blister, and crushing the first chamber to force the contents to enter the second chamber under pressure. The second chamber is preferably composed of a flexible blister material with the top inverted to minimize the volume of the second chamber prior to mixing. Breaking the seal and forcing the contents of the first chamber into the second chamber causes the top of the chamber to pop up or expand to accommodate the contents of both chambers. The second chamber, that contains or is adjacent a piercing mechanism is then crushed by a plunger to dispense the mixed composition. The multi-chambered dosage form for mixing components prior to dispensing can be essentially doughnut shaped, with one or more chambers encircling or partially encircling a central chamber, or they may be positioned in a side by side arrangement or even stacked.

This present disclosure can also be described in certain embodiments as a dosage form for delivery of a pharmaceutical composition, in which the dosage form includes a first dosage chamber containing a first component of the pharmaceutical composition, a second dosage chamber containing a second component of the pharmaceutical composition, and a dispensing chamber that includes a piercable membrane. The second dosage chamber and the dispensing chamber may be two separate chambers, or the same chamber. The piercable membrane is a section of the membrane that is designed to be pierced by a piercing mechanism or device. The piercable membrane may include an area that is weakened by scoring, or thinned, effective to inhibit production of loose pieces of the membrane during use as it is penetrated, and to promote a seal of the pierced membrane to outer walls of the piercing tip. The dosage form also comprises a seal, for example first delamination seal, that prevents mixing of the contents of the first dosage chamber with the contents of the second dosage chamber, and may comprise a second delamination seal that prevents mixing of the contents of the second chamber with the dispensing chamber. The dosage form may further comprise a permanent seal, wherein the permanent seal surrounds the outer perimeter of all the chambers, and in which the first and second delamination seals have less adhesion than the permanent seal, such that the first and second delamination seals delaminate under significantly less pressure than the permanent seal.

As used herein, the term "dosage chamber", which encompasses the term "dosage blister chamber", refers to a compartment of the disclosed dosage forms that contain a component or a portion of the final pharmaceutical composition. A dosage chamber can contain a liquid or a solid composition, to be mixed with other components to form the final pharmaceutical composition when the contents of the chambers are combined during or just prior to administration. A "dispensing chamber", which encompasses the term "dispensing blister chamber", refers to a chamber that includes a piercable membrane and can include an internal piercing mechanism. Delamination zones are seals that are designed to break or delaminate when pressure is applied to the chambers so that the contents of the chambers can be mixed.

Certain dosage forms of the disclosure have two dosage chambers separated by a delamination zone, or in certain embodiments by a high vapor barrier material such as aluminum foil, for example. Embodiments also include dosage forms with three, four, five, or more dosage chambers, the contents of all of which are mixed as the pharmaceutical composition is delivered. The chambers can contain liquids or solids in any combination, however, in preferred embodiments, the final pharmaceutical composition is in liquid form. In certain embodiments one or more or even all of the dosage chambers can contain the same composition, or aliquots portions of the same composition when the volume of a dose is too large to fit within a single dosage chamber. It is an aspect of the disclosure that the dosage chambers are separated from each other during storage by delamination zones, or by membranes that can be pierced by a piercing device or burst by pressure, such that the barrier is removed when pressure is applied to the chambers in a delivery device, and that the final delamination or designed membrane failure is effective to allow the completed composition to enter the dispensing chamber for discharge to the site of treatment.

The present disclosure can also be described, therefore, as a method for dispensing a pharmaceutical composition comprising two components, wherein the two components are mixed in the dosage form immediately prior to dispensing. The method includes providing a multi chambered dosage form where a first component is contained in a first, crushable chamber and a second component is contained in a second, expandable chamber containing an internal piercing mechanism and a discharge outlet, where the first and second chamber are separated by an adhesive seal. The method further includes providing a mechanical pressure to crush the crushable chamber, breaking the adhesive seal and forcing the contents of the crushable chamber into the expandable chamber; and providing a second mechanical pressure to the expandable chamber to pierce the expandable chamber with the piercing mechanism and force the contents of the expandable chamber through the piercing mechanism and out the discharge outlet; where at least one of the components is a liquid. The method can also include first and second chambers arranged in a strip containing multiple sets of adjacent sealed chambers such that one chamber can be collapsed causing its contents to flow into the next chamber until the contents of all adjacent chambers of one set have been mixed in a single chamber of that set while the contents of all the remaining sets are kept separated. The strip can be fed into a dispensing device that includes a first stage compression wheel or plunger to collapse the adjacent chambers of the dosage form into the primary chamber and then transport that primary chamber to a position where the contents are dispensed by the second stage plunger while leaving the remaining sets of chambers in their original separated state. The method can further comprise a dosage form with three chambers, in which the contents of the first and second chambers are mixed in a third chamber that is pierced with either an internal or external piercing mechanism to dispense the dose.

It is a further aspect of the disclosure that any of the delivery devices or dosage forms described herein can include an indicator that the contents of the device has been exposed to extreme or potentially damaging high or low temperatures or to radiation levels that can cause the ingredients within the dosage forms to degrade or become inactive. A device can include, for example, irreversible temperature sensitive products such as strips, dots, decals, or labels containing crystalline materials that undergo an irreversible color change upon exposure to a particular temperature. Indicators can be used with various temperature sensitivities to create a visual history of temperature maxima and/or duration that the product has experienced. An example of such products are commercially marketed under the trade name, Thermax®, for example. Alternatively thermal sensitive ink can be used in the manufacture of the packaging for any of the devices or products disclosed herein, or such ink can be incorporated into or printed on the housing of a device or dosage form. Similar indicators can be used for the disclosed delivery devices and dosage forms to indicate radiation exposure. Typical indicators that detect high energy radiation change color from yellow to red upon exposure to radiation such as gamma rays. Other indicators can be used to detect exposure to ultraviolet or electron beam radiation. Certain of such labeled devices will find particular use in military applications or in extreme environments including deserts, tropical climates, extreme cold climates or even for use in space travel.

It is a further aspect of the disclosure that certain delivery devices can include a marking device such that a mark is produced on the user when a dosage is dispensed into the nostril of the user. Such a device is particularly useful in environments or situations such as pandemics, biological or chemical agent release or exposure events, or in institutions such as military, medical, educational or penal institutions in which a large number of subjects are required to receive an intranasal dose and it is important to be able to quickly determine who has received a dose. A preferred marking refill tip is a replaceable tip with dosage form for a nasal dispensing device similar to devices described in FIGS. 30 and 31. The purpose of the tip is both to dispense medication and to leave an identifying mark on the person receiving the medication. This mark may be in the form of a visible, colored ink or an ink that is only visible under infrared or ultraviolet light. The mark can assist in assuring compliance with regulations, in reducing duplication of dosing, reducing the chance of a missed dosage, as well as other situations. The marking agent, such as ink can be color-coded, for example, or otherwise coded to indicate a particular dosage or medical ingredient that is administered to a subject.

Throughout this disclosure, unless the context dictates otherwise, the word "comprise" or variations such as "comprises" or "comprising," is understood to mean "includes, but is not limited to" such that other elements that are not explicitly mentioned may also be included. Further, unless the context dictates otherwise, use of the term "a" or "the" may mean a singular object or element, or it may mean a plurality, or one or more of such objects or elements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A is a perspective view showing the bottom of the device with the activation knob in the inactive position, FIG. 1B is an end view of the device and FIG. 1C is another perspective view in which the spray tip is shown.

FIG. 18 is a cross section view of a positive displacement dosage form.

FIG. 19 is a cross section view of a positive displacement dosage form during discharge.

FIG. 20 is a cross section view of a positive displacement dosage form discharged.

FIGS. 21A and 21B are views of a dosage form.

FIG. 32 is a cross section view of a dual medication blister dosage form.

FIG. 33 is a cross section view of a dual medication blister dosage form in mixing mode.

DETAILED DESCRIPTION

Figure 1A:
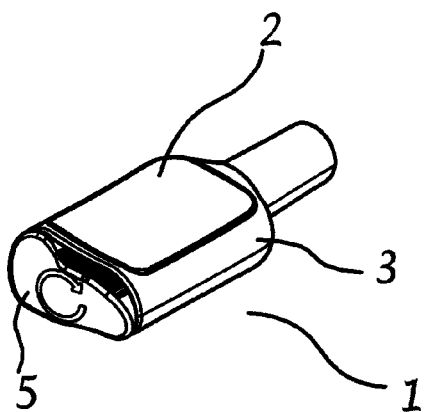
FIG. 1A-1C are different views of a device in the storage mode.
Figure 1B:
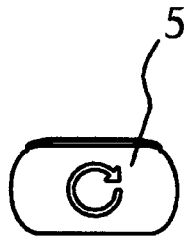
Figure 1C:
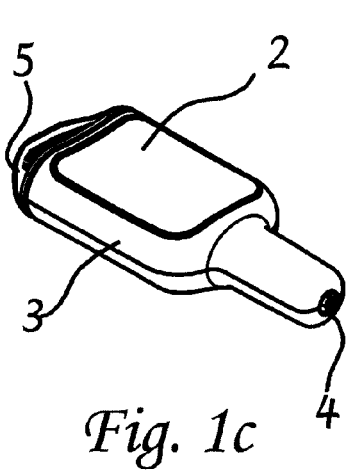
Figure 2A:
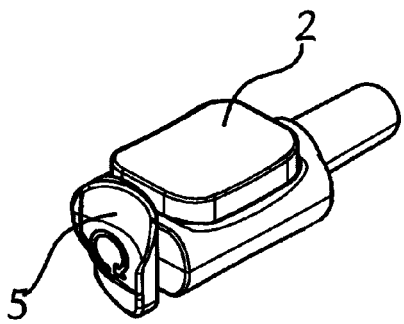
FIG. 2A-2C are different view of a device as shown in FIG. 1A-C in a ready mode.
Figure 2B:
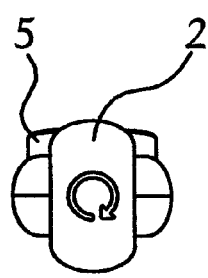
Figure 2C:
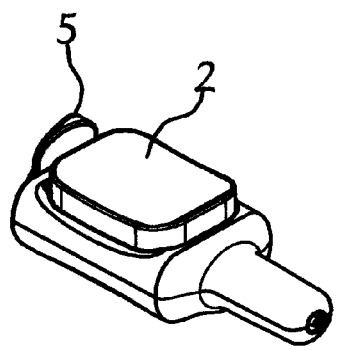
Figure 3A:
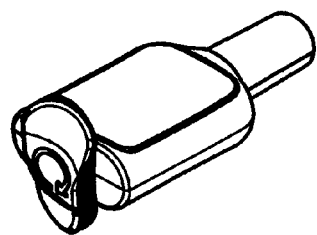
FIG. 3A-C are different views of a device as shown in FIG. 1A-C in fired mode.
Figure 3B:
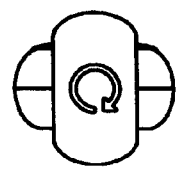
Figure 3C:
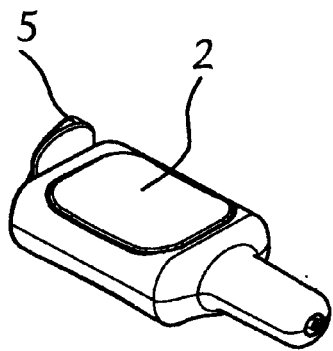
Figure 4:
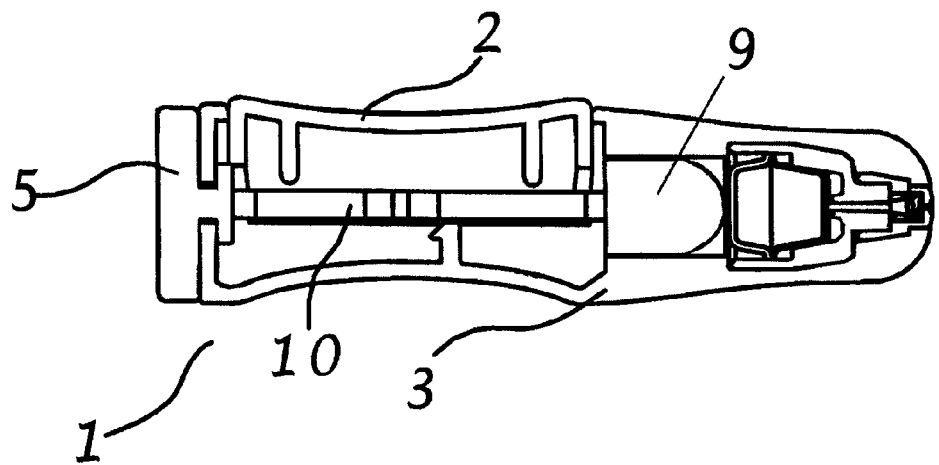
FIG. 4. is a cross section view of a device as shown in FIG. 1A-C in storage mode.

A preferred embodiment of an intranasal delivery device is shown in storage, ready and fired configurations in FIGS. 1, 2, and 3, respectively. The device 1 as shown, is a push button version of an intranasal delivery device. This embodiment includes a button 2, a body 3 with nozzle end 32 and an activation knob 5. The device shown in FIG. 1 is in storage mode, as can be seen by the positions of the activation knob 5, which is aligned with the body 3, and the button 2, which is in the depressed position. As shown, the activation knob 5, and the body 3, have a generally ovoid cross sectional shape. As used herein, when the activation knob 5 is in the storage position, the long axis of the activation knob 5 is aligned with the long axis of the body 3 cross section. A cross section of the push button device in storage position is shown in FIG. 4. In this view, the linkage 10 is horizontal under the button 2. The plunger 9 is in the retracted mode.

The embodiment of an intranasal delivery device shown in FIG. 1 is shown in FIG. 2 in the ready or activated mode. In the ready mode, the activation knob 5 has been rotated 90° moving the internal mechanism into the dispensing position and raising the button 2. Although in the device shown in the figures, the activation knob is turned clockwise in order to place the device in ready mode, it is understood that the knob could also be configured to turn counterclockwise with the same effect. The device in ready or activated mode is shown in cross section in FIG. 5. The linkage 10 is attached at one end to the activation knob 5, and at the opposite end the linkage engages or is attached to a plunger 9. Rotation of the activation knob 5 rotates the linkage 10 causing it to contact the button 2, and to push the button into the raised or ready position. In certain embodiments, an audible click or snap indicates that the device is ready to dispense. The linkage 10 is made of any appropriate material that is semi rigid to provide the necessary mechanical strength, and is cost effective for use in a disposable device. The material is typically a polymer or metal with flex points indicated at points 10a, 10b & 10c. The activation knob 5, linkage 10, and plunger 9 may all be made as a single piece or as two or more pieces that are assembled during assembly of the device.

The nozzle end 32 designed for insertion into the nostril of a user, also provides an internal channel that contains the plunger 9, and a cavity designed to contain the dosage form 60 containing medication 62, and the external piercing mechanism 6. The piercing mechanism includes a piercing tip 8 and discharge channel 7 in fluid communication with the outlet 4.

Figure 6:
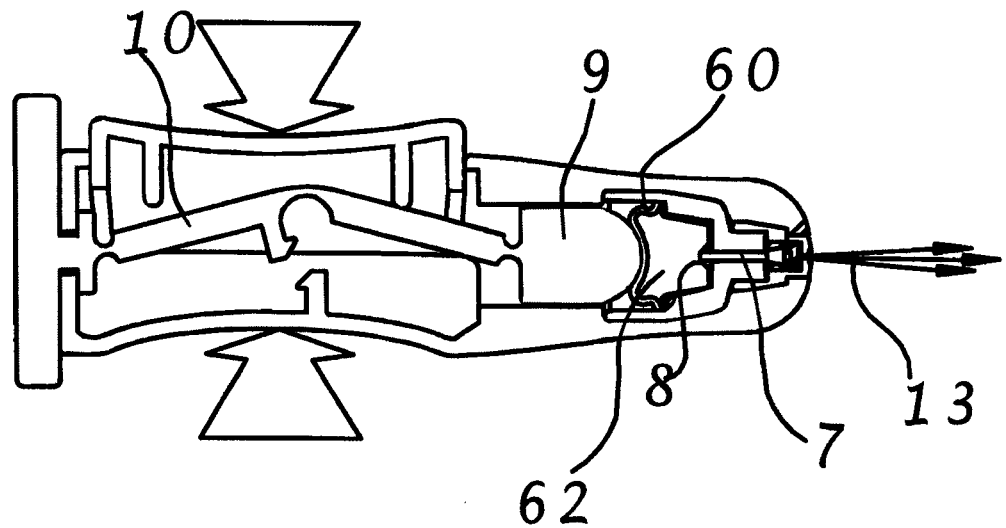
FIG. 6 is a cross section view of a device as shown in FIG. 2A-C during discharge.

FIG. 6 shows the device during dispensing. Pressing down on the button 2 transfers force to the flex point 10b of the toggle linkage 10. The force is then transferred to the plunger 9, driving it and the dosage form 60 forward. The dosage form 60 moves forward until it is pierced by the piercing tip 8. Then the plunger 9 continues to move forward collapsing the dosage form 60 and expelling the medication 62 out the discharge channel 7 in the form of a spray 13.

Figure 7:
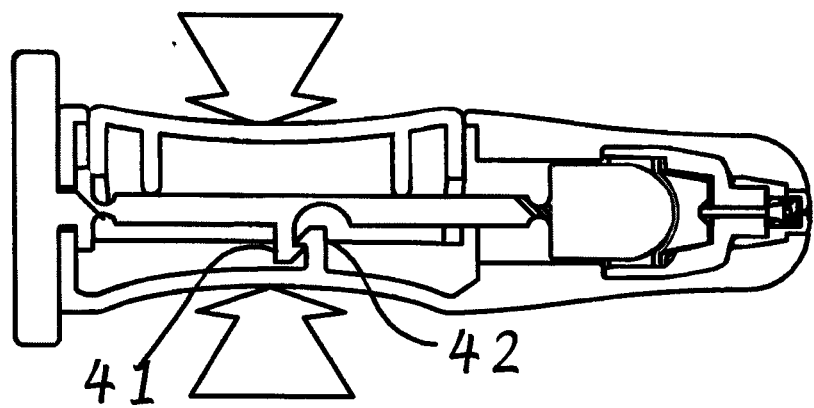
FIG. 7 is a cross section view of a device as shown in FIG. 3A-C in discharged/locked mode.

The device is shown in the fired or dispensed mode in FIGS. 3 and 7. The activation knob 5 is still in the vertical orientation and the button 2 has been fully depressed, the medication 62 dispensed and the toggle linkage 10 locked in the fired position. The locking of the toggle linkage is accomplished by the upper latch 41 being pressed past the lower latch 42 into a locking interference, preventing the device from being re-charged or re-used.

Figure 8:
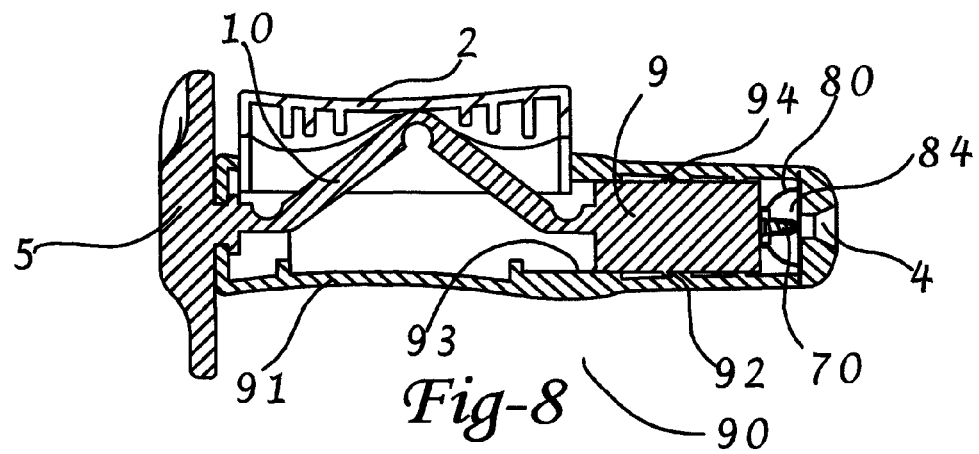
FIG. 8 is a cross section view of a device with an internally pierced dosage form.

Certain embodiments of the present disclosure are designed for use with an internally pierced blister 80. An example of such a device 90 is shown in FIG. 8. The blister 80 contains medication 84 and a piercing nozzle 70. Device 90 includes a body 91 and nozzle end 33, designed for insertion into the nostril of a user. The nozzle end provides a cavity for the plunger 9 and blister 80. The embodiment shown also includes an activation knob 5, linkage 10, plunger 9 and button 2 as in the previously described device 1. The button has an outer surface and an inner surface. The inner surface 37 forms a channel configured to receive the linkage 10 when the activation knob rotates the linkage against the button, raising it to the ready position. This channel in the inner surface 37 of the button holds the linkage in place against the button so the linkage doesn't slip when the button is pushed to fire the device. In the embodiment shown in FIG. 8, the plunger 9 has a detent 94 that imposes on a rib 92 on the bore 93 of the nozzle end 33 of body 91. The device 90 is activated and dispensed in the same manner as described for device 1. In the present embodiment, however, the rib 92 interferes with the detent 94 and resists the forward motion of the plunger 9 until sufficient pressure is developed to force the plunger detent 94 past the rib 92. This restriction insures that enough force has been generated to drive the plunger 9 into the blister 80 and to produce an internal pressure sufficient to create the desired spray pattern 13.

Figure 9:
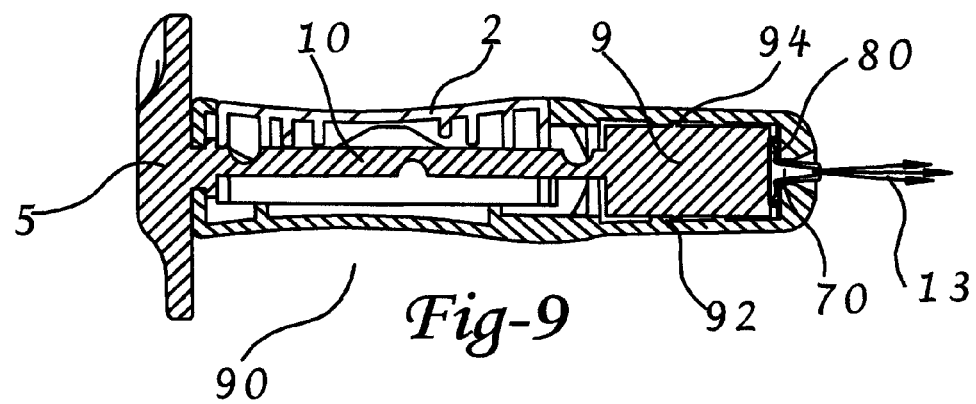
FIG. 9 is a cross section view of a device with an internally pierced dosage form in discharged mode.

FIG. 9 shows the device 90 in the fired mode. The plunger 9 compresses the blister 80 almost completely resulting in a more complete and accurate dispensing of the medication 84. It is understood that the linkage 10 can be locked in the fired position as shown for device 1. Additionally, the detent 94 can be made to lock when moved past rib 92 and to hold the plunger 9 in the fired position, thus preventing re-use of the device.

Figure 10:
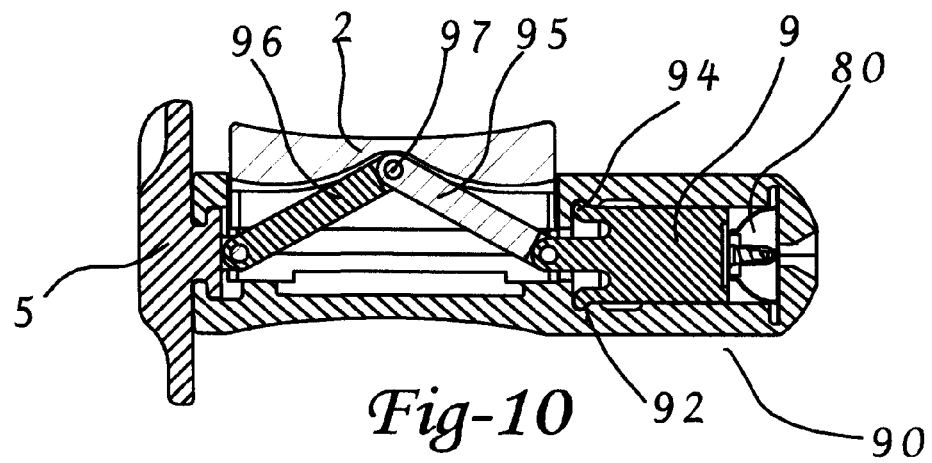
FIG. 10 is a cross section view of a device with a pin-type toggle mechanism.

An alternative embodiment of device 90 is shown in FIG. 10. In the device shown in FIG. 10, the linkage is a pinned toggle mechanism, including a forward link 95, a rear link 96 and hinge pin 97. This type of linkage could also be used with an externally pierced dosage form as described above. An alternative configuration of the detent 94 and rib 92 are also shown in FIG. 10 and again function to ensure that sufficient pressure is applied to the button to release the contents of the blister in the desired spray pattern.

Figure 11:
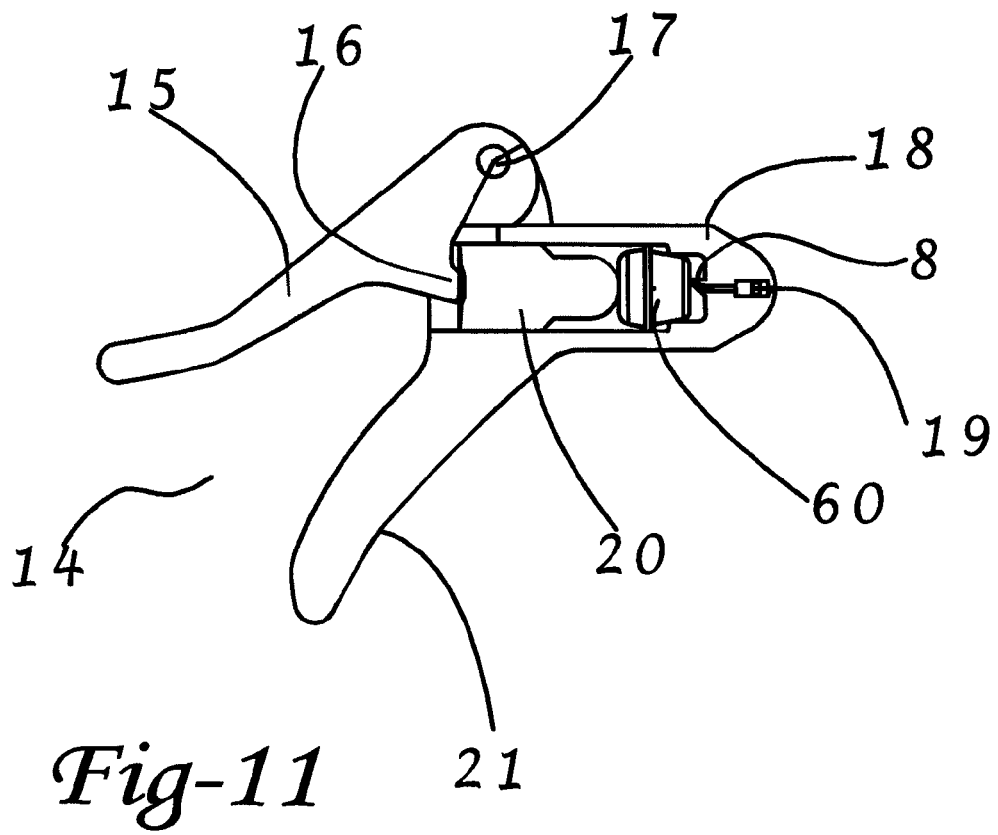
FIG. 11. is a cross section view of a pivot device in ready mode.

An alternative embodiment of an intranasal delivery device is shown in FIG. 11. This embodiment includes a pivoting firing device. This device 14 includes a body 18 and pivot arm 15, attached to the body at the forward end of the pivot arm. The pivot arm includes a projection, the pivot ram 16, that extends into the body 18 and contacts the plunger 20. The plunger is positioned to crush the dosage form 60 containing fluid medication. The body 18 provides a discharge nozzle 19 in fluid communication with the discharge channel 34, and piercing tip 8, that is opposite the plunger and is effective to pierce the dosage form when the device is activated and the plunger crushes the dosage form against the piercing mechanism. The device is designed to be held in one hand of a user with the fingers or one or more fingers on the top of the pivot arm and the thumb of the same hand on the bottom of the grip arm 39. The lower surface of the grip arm 39 provides a thumb grip area 21. The device is fired by holding the device as indicated and squeezing the fingers and thumb together, thus driving the plunger into the dosage form and discharging the medication. This embodiment can also be provided with a detent and rib structure in order to lock the fired mechanism and prevent reloading or re-use.

Figure 12:
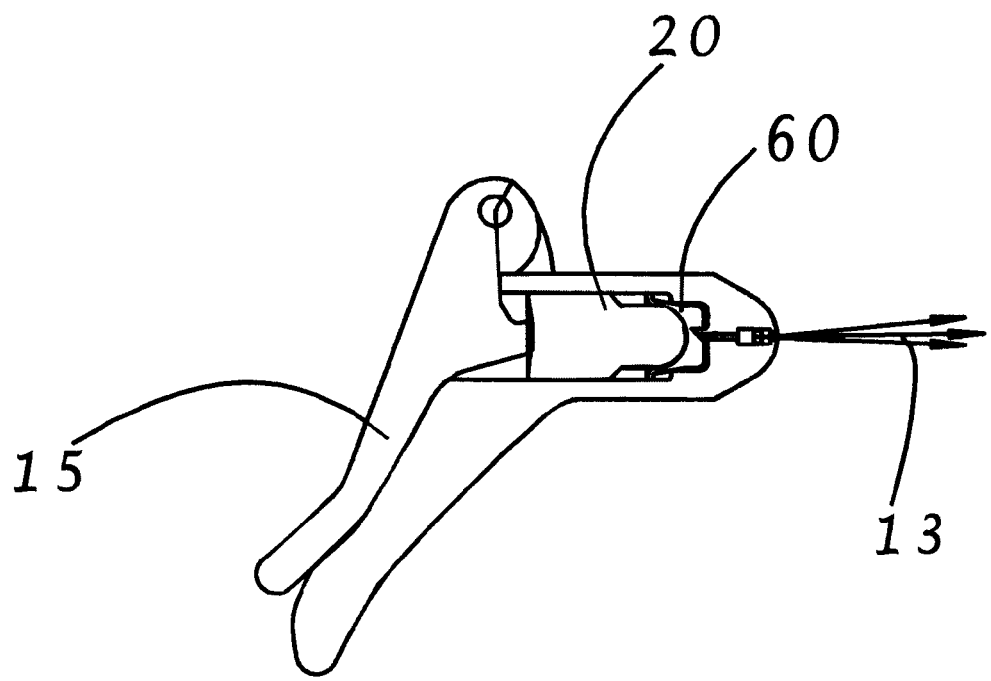
FIG. 12. is a cross section view of a pivot device in fired mode.

FIG. 12 is an illustration of the device 14 while dispensing medication. In the illustrated embodiment, mechanical advantage is provided by the action of the pivot arm 15 pivoting around the pivot point 17 and driving the pivot ram 16 to move the piston body 20, or plunger. Moving the piston body 20 forward pierces the dosage form 60 on the piercing tip 8 and compresses the dosage form 60 causing the medication to be discharged in a spray 13. The device may also incorporate a lock or latch mechanism such that when the device has been fired, the pivot arm cannot be moved back into the raised, ready position, or alternatively, the piston body may be locked in the fired position such that the piston body cannot be returned to the ready position without breaking the device.

Figure 13:
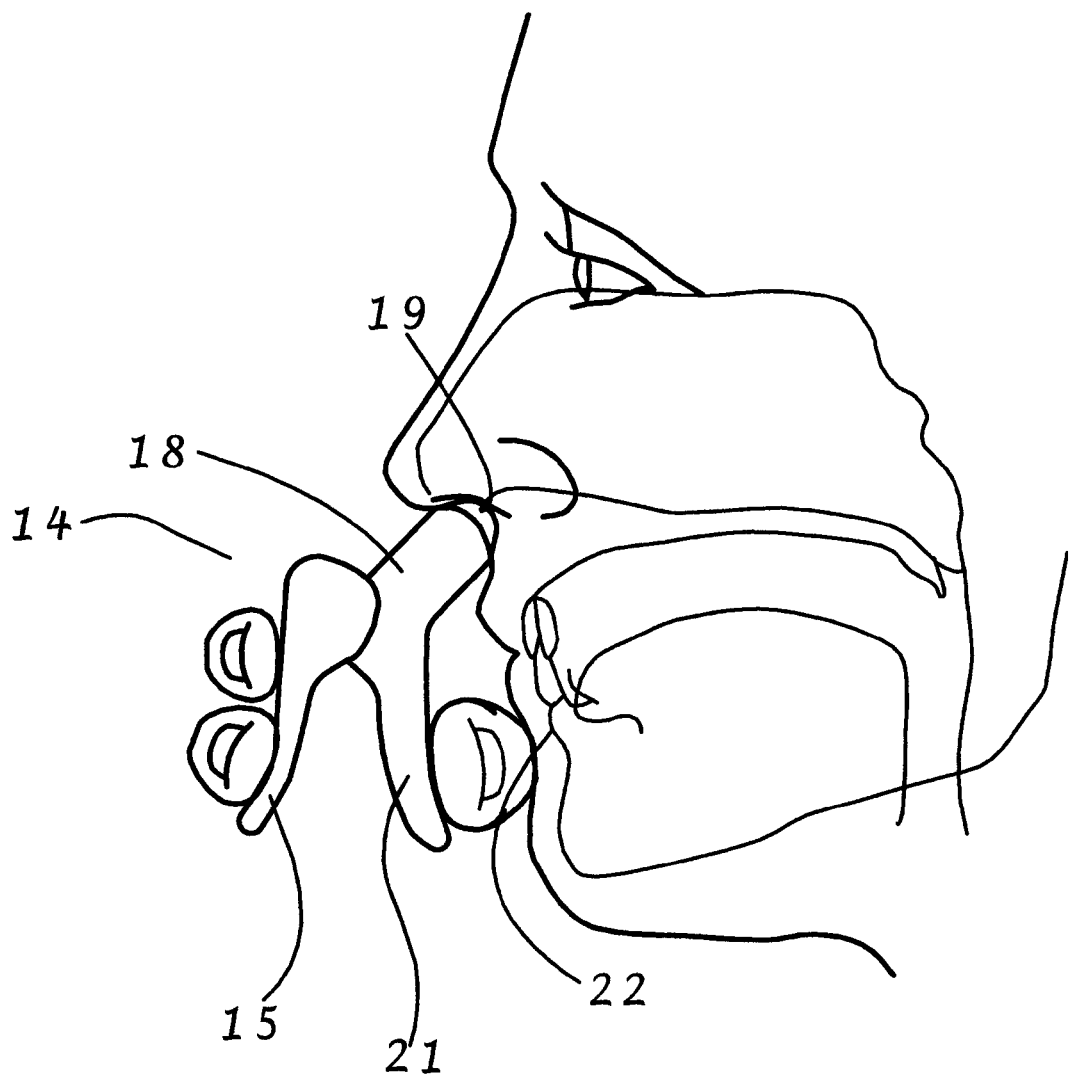
FIG. 13 is a drawing of the use of pivot device to direct a discharge into the nasal passage.

An aspect of intranasal drug delivery devices as disclosed herein is delivery of the correct droplet size to the correct location. Droplets of 50 μm may be too large to penetrate the nasal cavities and droplets of less than 5 μm may pass directly into the lungs without being absorbed in the nasal mucosa. Up to 90% of the drug delivered using by conventional spray pumps is deposited in the anterior chamber of the nasal cavity then quickly cleared and swallowed. Doses are not consistent due to a poor user interface and variable spray characteristics. An aspect of the present disclosure is embodiments in which the device is correctly aligned for optimal delivery of drug to the nasal mucosa. For example, the device shown in FIG. 11 includes an alignment feature to direct a user to correctly deliver the drug. This alignment is demonstrated in FIG. 13. When the patient's thumb is positioned against the thumb grip area 21 of the body 18 and then placed in the depression in the chin below the lower lip 22 and the discharge nozzle 19 is placed in the patient's nostril, the discharge nozzle 19 is aimed at the correct area of the nasal passage for proper absorption of the fluid medication. Furthermore, positioning the thumb in the depression below the lower lip 22 steadies the device such that depression of the pivot arm 15 dispenses the fluid medication without changing the direction of the spray away from the desired location in the nasal passage.

Figure 14:
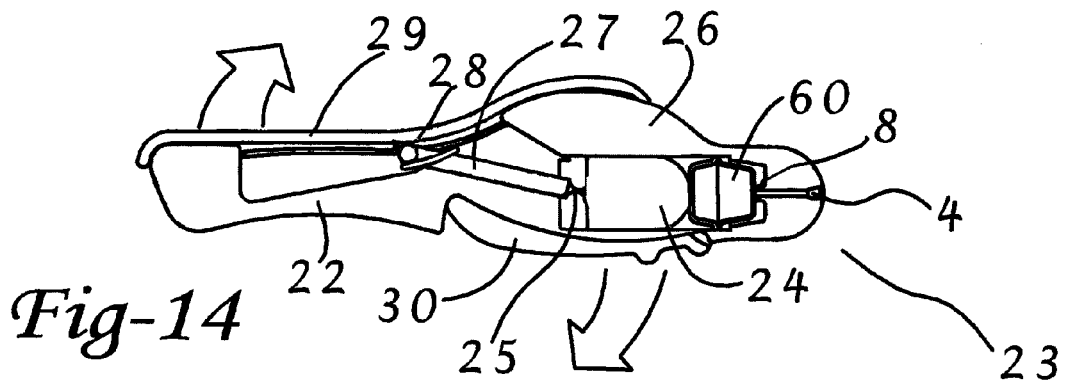
FIG. 14 is a cross section view of a lever in stored position.

Another embodiment of an intranasal delivery device is shown in FIG. 14 in storage mode. This embodiment utilizes a lever mechanism to deliver the drug and to provide a mechanical advantage to the user. The device 23 includes a body 26 and a lever arm 29, shown in the retracted position against the body on the surface opposed to the thumb grip area 22. The lever arm is connected at one end of link 27, and the piston body or plunger 24 is connected to the opposing end of the link at attachment point 25. The illustrated device contains a dosage form 60 containing fluid medication and an external piercing mechanism as previously described with a piercing tip 8 and delivery channel to a discharge nozzle 4. This device also includes a bite arm 30, used to correctly position the device for effective drug delivery and to cause closing off of the back of the throat to direct the drug to the nasal mucosa. The device shown in storage mode has both the lever arm 29, and bite arm 30 in the retracted position.

Figure 15:
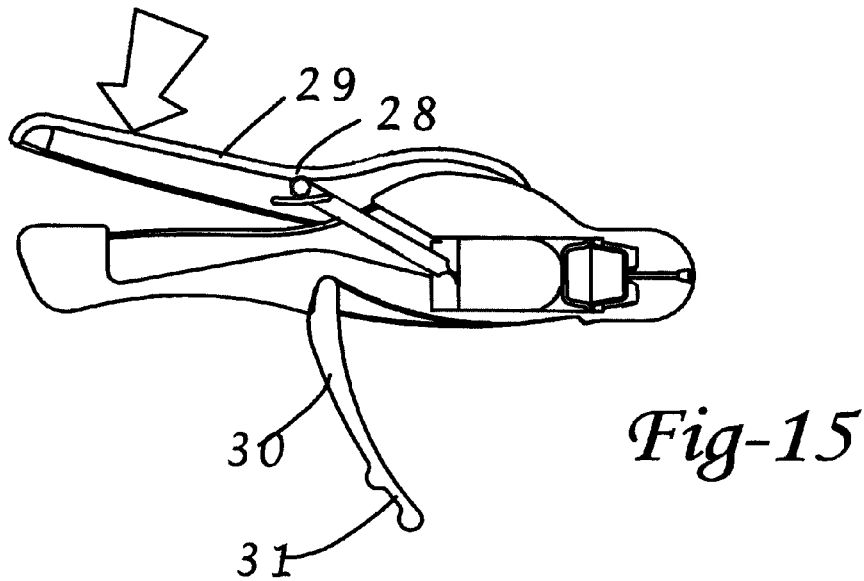
FIG. 15 is a cross section view of a lever in ready position.
Figure 17:
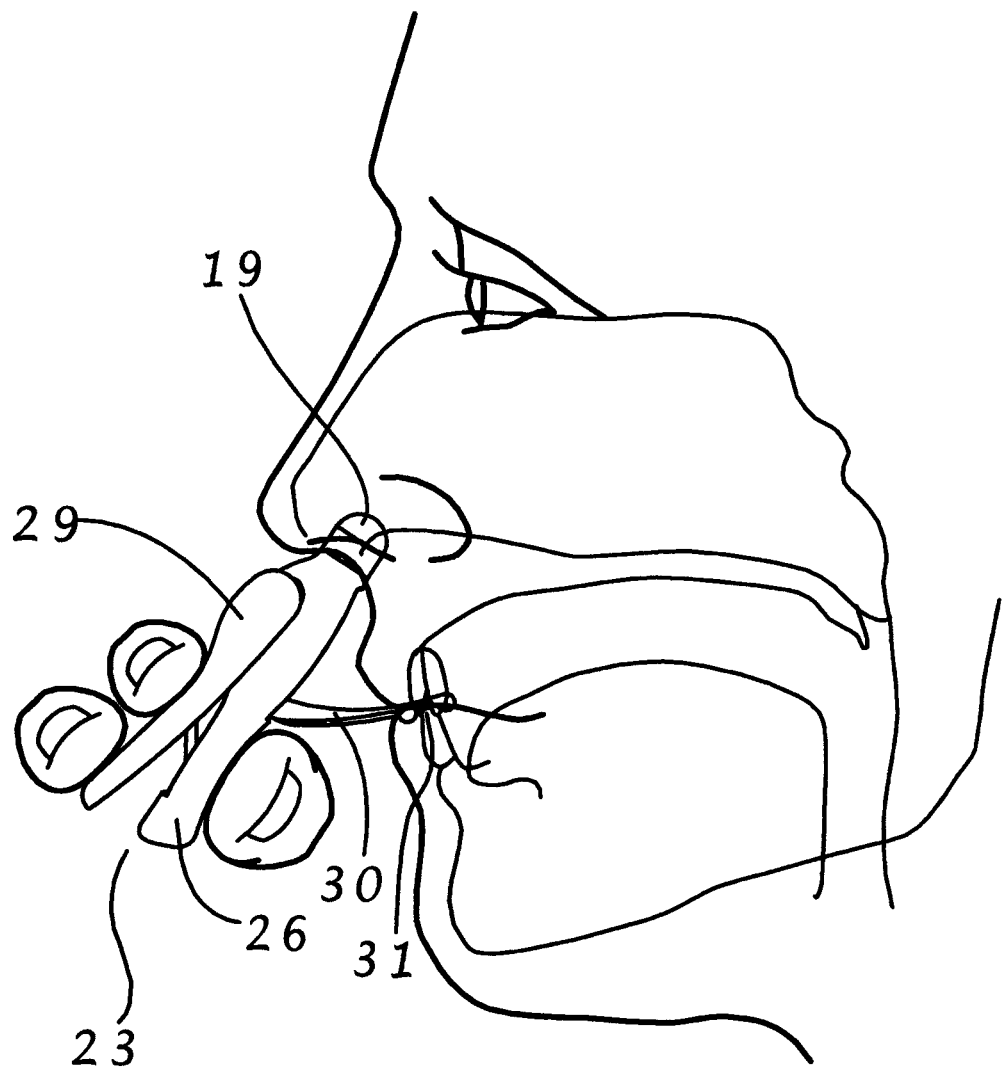
FIG. 17 is a drawing of a user with the lever device positioning the device for discharge into the nasal passage.

FIG. 15 shows the device 23 activated for use. In this mode, the lever arm 29 is raised to the activated position causing the link 27 to engage the notch 28. In the embodiment shown, A pin 38 slides forward in a hinge along the lever arm 29 until the linkage engages the notch. Additionally, the bite arm 30 is moved down to the position shown. The bite arm 30 contains a bite area 31 used to correctly align the device. The use of the bite arm is illustrated in FIG. 17. When the bite area 31 is placed between the teeth and the discharge nozzle 19 is placed in the nostril, the discharge nozzle 19 is aimed at the correct area of the nasal passage for proper absorption of the fluid medication. Furthermore, positioning the bite area in the teeth steadies the device such that depression of the lever arm 29 dispenses the fluid medication without changing the direction of the spray away from the desired location in the nasal passage.

Figure 16:
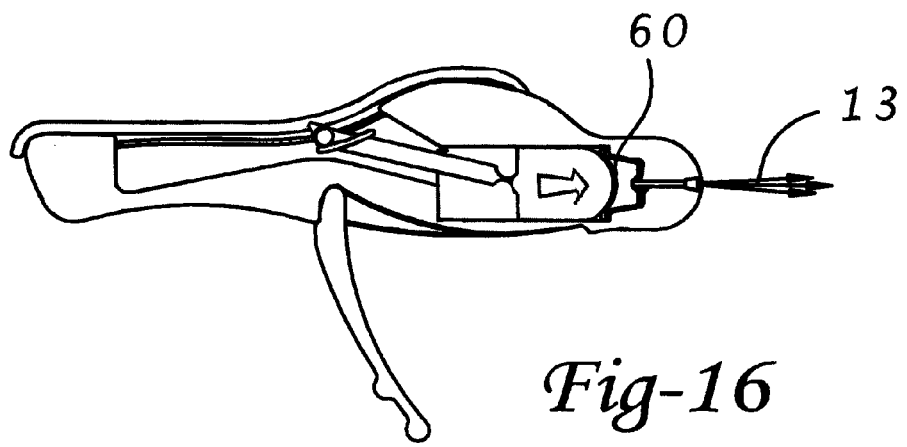
FIG. 16 is a cross section view of a lever in discharged position.

FIG. 16 shows the device 23 in the dispensed mode. Depressing the lever arm 29 back to the original position causes the link 27 to drive the piston body 24 forward, piercing the dosage form 60 on the piercing tip 8, compressing the dosage form 60 and causing the medication to be discharged in a spray 13.

An aspect of the present disclosure is the dosage forms to be used in the described delivery devices. FIG. 18 illustrates a positive displacement dosage form 50 including an outer body 51, a thin membrane 52, and an inner chamber 56 that contains the fluid or drug to be administered. Also shown is a complementary piercing mechanism 54, that provides a piercing feature 53 and discharge channel 55. The delivery of the drug contained in the dosage form is demonstrated in FIGS. 19 and 20. When used in a device as described herein, a piston presses the dosage form and moves it against the piercing mechanism. This force causes the piercing feature 53, which may be a needle-like object to penetrate the thin membrane 52, allowing the liquid to pass into and through the discharge channel 55 to create the desired spray discharge 13.

FIG. 20 shows the dosage form 50 completely collapsed. An important feature of the positive displacement dosage form is that the piercing body 54 is so matched to the interior geometry of the dosage form body 51 that it displaces virtually all the interior volume of the dosage form 50.

A top view and a section view at line A-A of an externally pierced dosage form 60 is shown in FIG. 21. The dosage form 60 includes an interior chamber 62 which holds the fluid medication until the time of dispensing and a thin membrane or film 61 designed to rupture around the piercing tip of the various intranasal delivery devices. The dosage form further includes a parting line 63 where the dosage form halves are sealed around the fluid medication.

Figure 22:
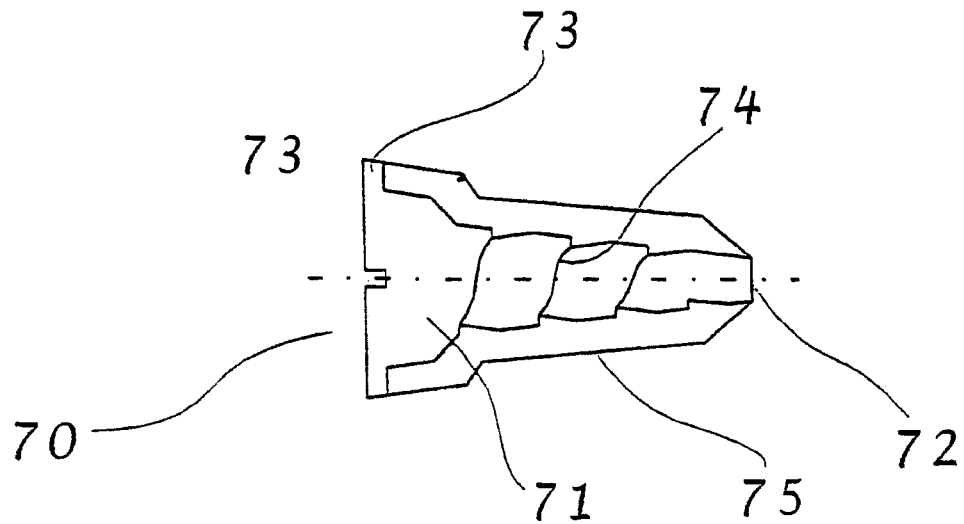
FIG. 22 is a cross section view of a piercing nozzle.

An embodiment of a piercing nozzle 70 used to pierce the dosage form, control the flow of fluid and control the spray pattern and droplet size is illustrated in FIG. 22. The nozzle includes an inner chamber 71 with openings at each end, a piercing tip 72 and a plurality of inlet openings 73. The presence of steps, flutes, ribs and other features 74 on the surface of the inner chamber 71 has been demonstrated to control the spray pattern and droplet size of the fluid flowing through the nozzle. For example, vortexing can be controlled by spiral cuts, conically tapered holes, flow routing channels, and other means known to those of skill in the art. Droplet size can be controlled by factors such as exit hole geometry (length, diameter, angle) or pressure buildup, through controlling the force required to puncture the blister. It is understood that the geometry and droplet sized for the discharge spray from the described devices can be controlled by matching the features of the nozzle to the viscosity of the fluid to be dispensed and that the design of the nozzle will vary according to properties of the fluid.

Since the rate and method of absorption of various fluid medications are influenced by the droplet size and distribution inside the nasal cavity, it is beneficial to control this spray pattern. The surface features 74 can be designed for different types of spiral, vertical and other flow and the design can be adjusted for different viscosities of the fluid to be dispensed. For example, surface features may be added to create a vortex, to further mix the contents of the blister, to change the fluid property type from laminar to turbulent or vice versa or to change fluid properties such as pressure, velocity, surface tension or viscosity. This use of surface features to control spray pattern can also be applied to the discharge passage 55 of the piercing body 54 of the positive displacement dosage form 50 described earlier.

Figure 23:
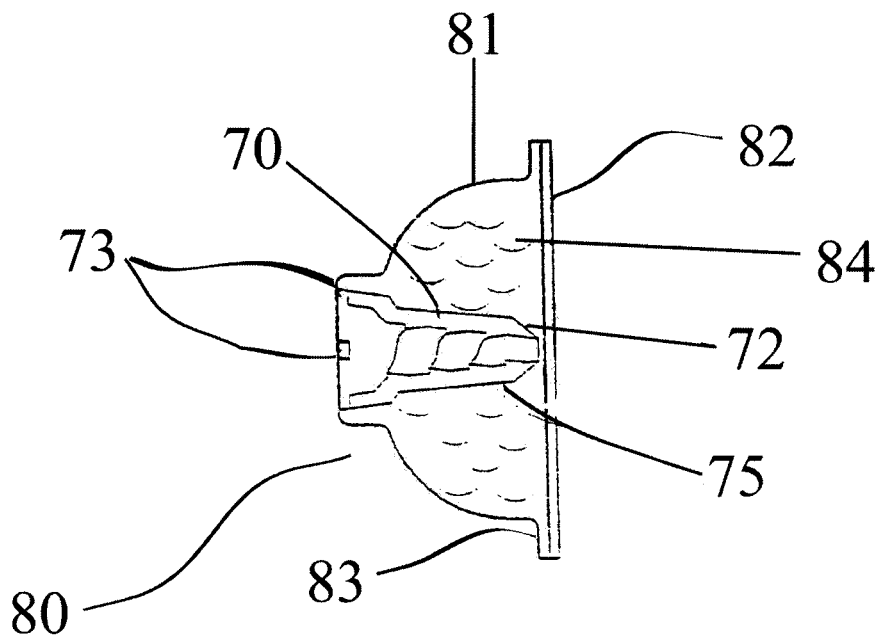
FIG. 23 is a cross section view of an internally pierced dosage form.

An embodiment of an internally pierced dosage form 80 containing a piercing nozzle 70 inside is illustrated in FIG. 23. The dosage form 80 is constructed of a dome-like blister 81 made of flexible material and a pierceable surface 82. The blister and pierceable surface have a circumferential seal 83 allowing the containment of a fluid 84 and the piercing nozzle 70. When the internally pierced dosage form 80 is compressed from the direction of the pierceable surface 82, the piercing tip 72 penetrates the pierceable surface 82. As the internally pierced dosage form 80 is further compressed, the outer surface 75 of nozzle 70 forms a seal against the pierceable surface 82, the fluid 84 contained in the blister is forced to flow through inlet openings 73 and out the opening in the piercing tip 72. This path produces two 90° turns in the flow of the fluid, the first as the fluid, moving in a downward direction away from the pierceable surface enters the inlet openings, and the second when the fluid then enters the delivery channel through the center of the piercing tip. This fluid movement improves the control of the flow and droplet size during dispensing.

Figure 24:
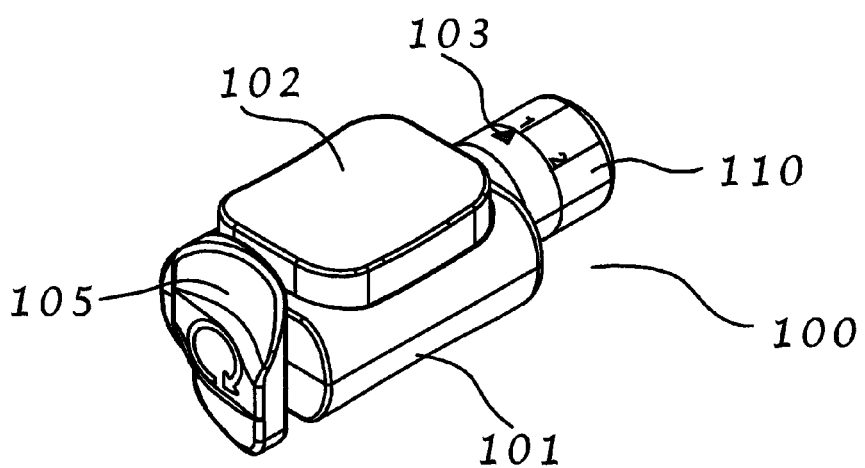
FIG. 24 is a perspective view of a Bi-dose push button dispenser in a first position.
Figure 25:
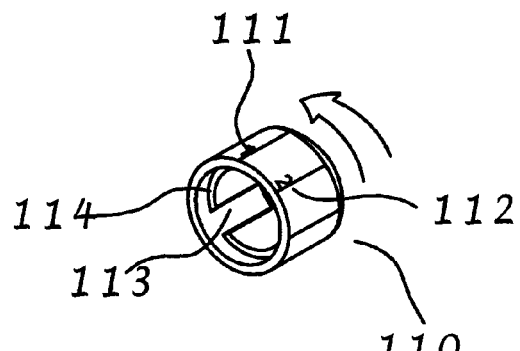
FIG. 25 is a perspective view of a rotatable tip used on the device as shown in FIG. 24.
Figure 26:
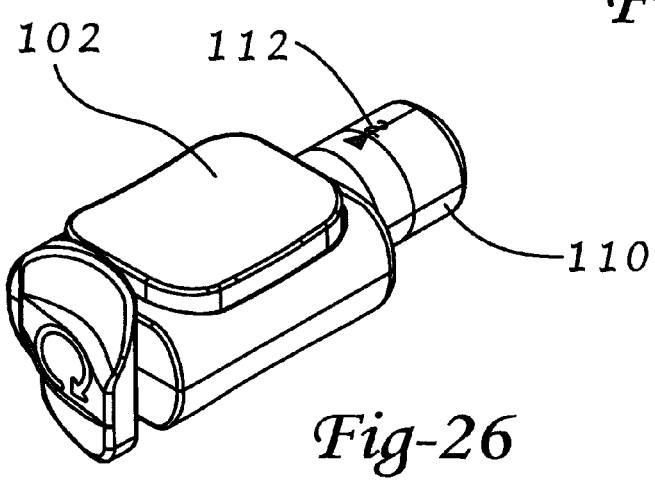
FIG. 26 is a perspective view of a Bi-dose push button dispenser in a second position.

Certain embodiments of the disclosure are designed to deliver a dose of medication in two increments, as a user might deliver one half dose to each nostril, for example. Such a device is termed a bi-dose device 100 as shown in FIG. 24. The example shown in the figure includes a body 101, a button 102, and an activation knob 105 that can function as in the single dose push button devices described above. The nozzle end of device 100 includes a rotatable tip 110. The device body includes an arrow or other mark as a position indicator 103 and the rotatable tip includes indicators for a first position 111 and a second position 112. The numbers 1 and 2 can be used for the first and second positions, respectively, as in the example shown, but it is understood that any other numbers, symbols, letters, or even colors could be used to indicate the correct alignment of the rotatable tip for administration of each of the two half doses. The tip 110, which is a hollow cylinder includes an internal shoulder 114 proximate the edge that adjoins the body of the device, and further includes one or more channels 113. In the example shown there are 2 channels disposed in 180° opposition along the length of the tip, but various numbers of channels and configurations are also contemplated. Rotating the tip 110 in the direction of the arrow moves the internal channels 113 to a predetermined position, the top and bottom positions inside the tip in the example shown in the figures. FIG. 24 shows the device with the rotatable tip in the first position and FIG. 26 shows the device with the rotatable tip in the second position.

Figure 5:
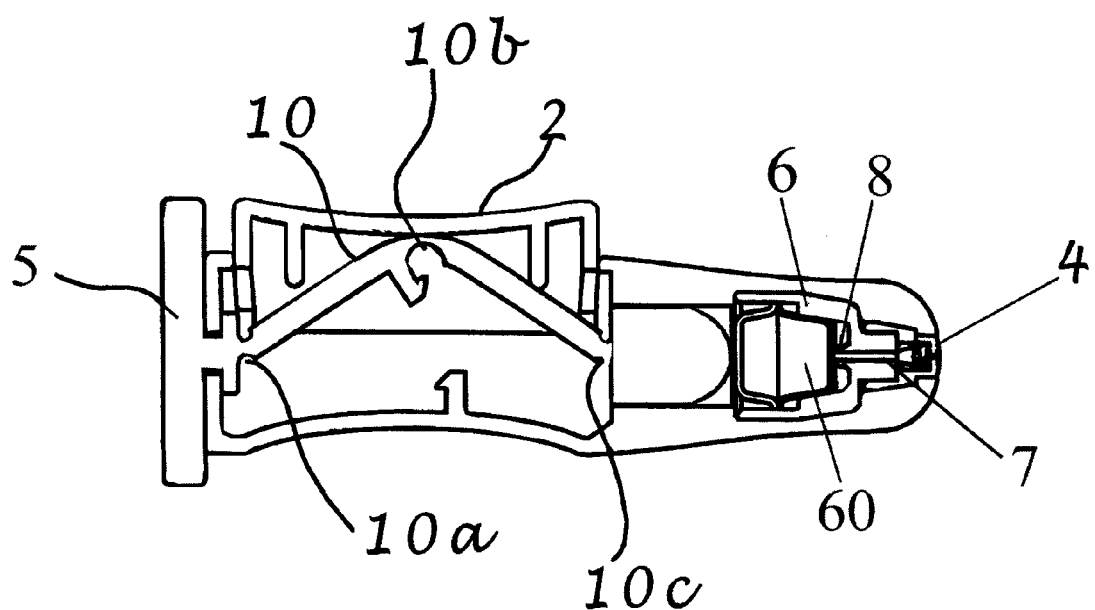
FIG. 5. is a cross section view of a device as shown in FIG. 2A-C in ready mode.
Figure 27:
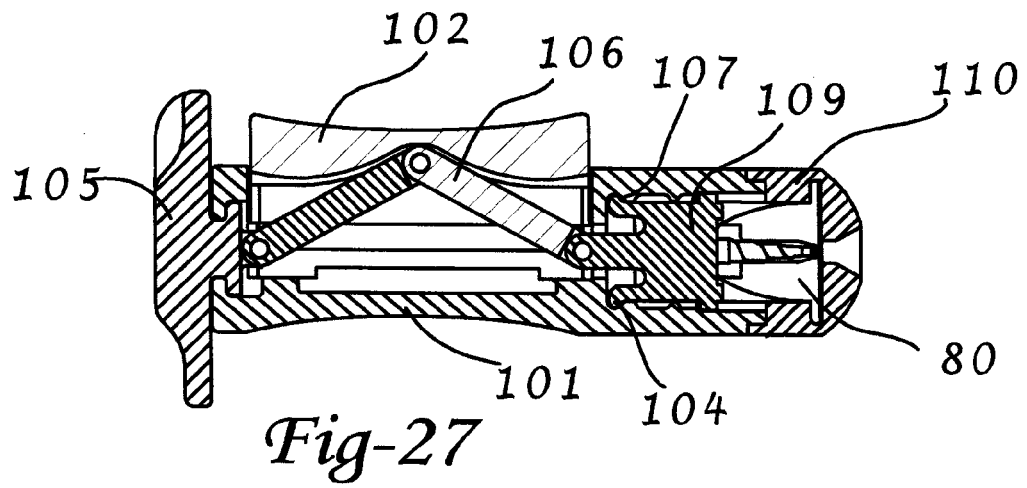
FIG. 27 is a cross section view of a Bi-dose push button dispenser in the first position.
Figure 28:
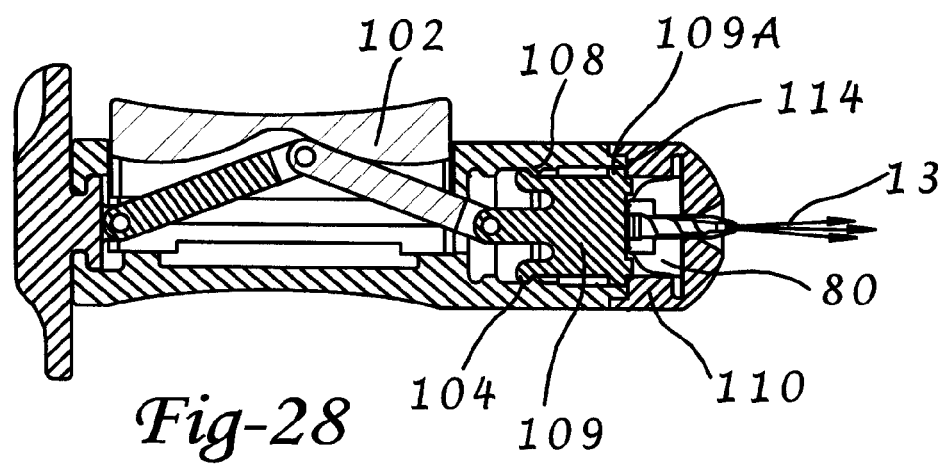
FIG. 28 is a cross section view of a Bi-dose push button dispenser during discharge.
Figure 29:
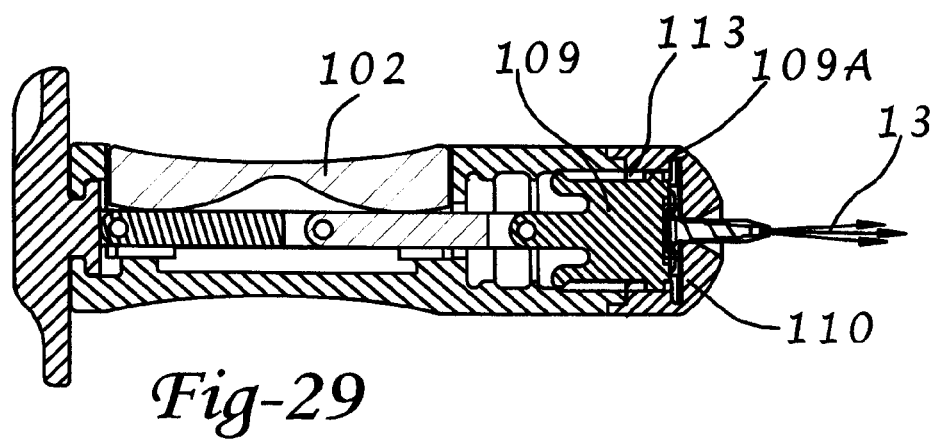
FIG. 29 is a cross section view of a Bi-dose push button dispenser that has been discharged.

FIG. 27 shows Cross section views of the device 100 are shown in FIGS. 27-29. The device in FIG. 27 is in ready mode as previously described. Activation knob 105 is rotated to the vertical position raising the button 102 to the ready position. The device 100 uses the previously described method of actuating the linkage 106 to drive the plunger 109 and dispense medication from the internally pierced blister 80. It is understood that the internally pierced blister is used by way of example only, and that an externally pierced dosage form could also be used in a bi-dose dispenser. The linkage may be a single piece as shown in FIG. 5 or the multi piece jointed linkage shown in FIG. 10 or FIG. 27. The plunger 109 shown in the present example includes a detent 104 which rests, in the ready position, against a rib 107 formed in the internal surface of the nozzle, formed to resist motion of the plunger 109 past the rib until adequate pressure has been developed to insure a proper spray pattern.

FIG. 28 shows the device 100 after dispensing the first dose of medication. The plunger 109 has moved forward until the tab 109A lands against the shoulder 114 of the tip 110. The shoulder 114 prevents the plunger 109 from moving any further in the forward direction. After administration of the first dose, the button is only partially depressed and is ready to be fully depressed to dispense the second dose. Additionally, the detent 104 has moved to rest on a second rib 108. In order to prepare the device for dispensing the second dose, the tip is rotated to the second position. This rotation moves the one or more channels formed in the interior of the tip into alignment with the same number of tabs 109A formed on the plunger. Thus the shoulder portions of the tip have moved away from the tabs and no longer prevents forward movement of the plunger, which is still inhibited by detent 104 resting against the second rib 108.

FIG. 29 shows the device 100 after dispensing the second dose of medication. When the button 102 is pushed with enough force to overcome the resistance of the detent 104 against the rib 108, the plunger 109 moves forward and completely collapses the blister 80, dispensing the second dose of medication with sufficient force to create the desired spray pattern.

Figure 30:
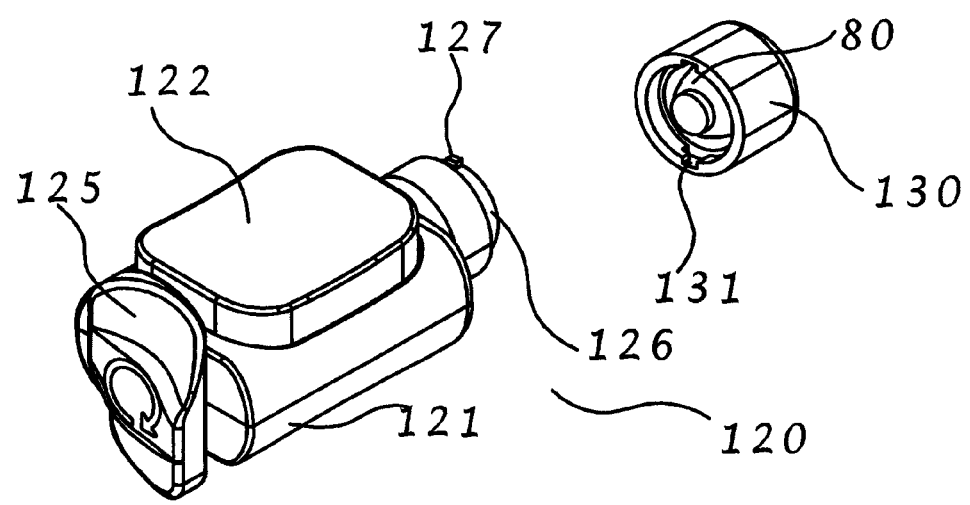
FIG. 30 is a perspective view of a push button dispenser with replaceable dosage form.
Figure 31:
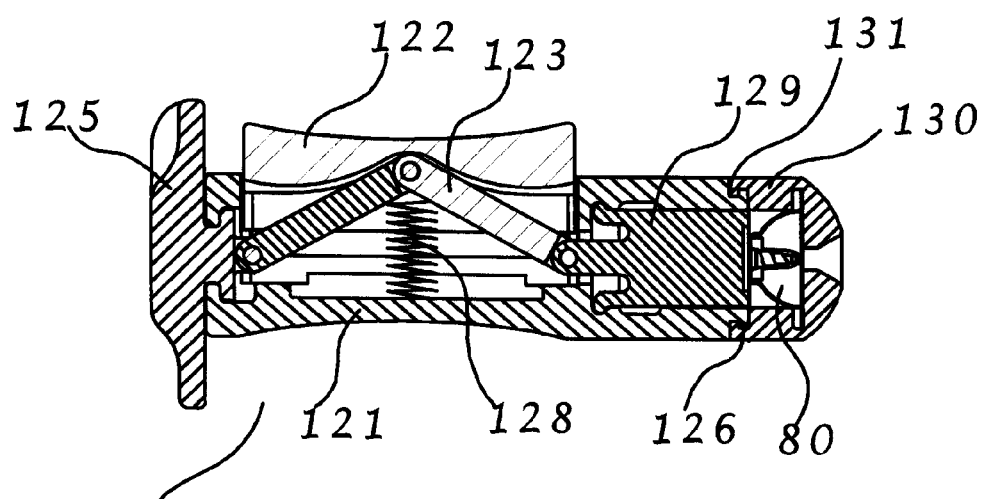
FIG. 31 is a cross section view of a push button dispenser with replaceable dosage form.

An embodiment of the present disclosure is re-usable device, an example of which is shown in FIG. 30. The re-usable device 120 is shown as a push button device, although any of the devices described herein are contemplated to be adapted to be re-usable. The device includes a removable and replaceable tip 130 with bayonet fitting 131 and blister 80. Other types of fittings are also contemplated, including but not limited to friction locking, threaded surfaces, camming surfaces and the like. The tip 130 in the example shown can be attached to the front of the device 120 by slipping it on the protrusion 126 and twisting the tip 130 to engage the tabs 127 on the body. After dispensing the medication contained in the tip 130, the tip and empty blister can be removed by twisting in the reverse direction and another tip with full blister can be attached to the device. FIG. 31 shows a cross section of the device 120 in the ready mode. The device can include a detent 155 and rib 156 to ensure that sufficient force is applied to the button to create the desired spray upon firing the device. In certain embodiments, a spring 128 is provided to reset the linkage 123 and button 122 to the ready mode after use. The activation knob 125 can also be rotated 90° counterclockwise to place the device in safe mode.

FIG. 32 illustrates an embodiment of a dual medication blister 140. In some cases it is desirable to mix two medications just before dispensing. An example of such applications is the use of a freeze-dried active agent that is re-hydrated in the blister just prior to administration. Other examples are drugs that are unstable in the solvent or carrier that could be stored separately until just prior to dispensing. salicylic acid or aspirin is one such drug that is unstable in saline and could be stored in dry form and mixed in the blister prior to dispensing. The blister 140 includes a central chamber 141 and a surrounding chamber 142. The central chamber contains the first medication and may be of a powder or liquid form. The surrounding chamber, which is an annular, or doughnut shaped chamber, contains a second liquid medication or activating ingredient. The flexible skin 143 of the central chamber is formed in an inverted manner allowing it to expand or pop out to a larger volume. The seal 144 between the two chambers is of a light adhesion such that it can be separated without damaging the skin material and without separating the outer seal 145. The plunger mechanism has two stages. The outer plunger 151 can advance independently of the inner plunger 152.

Figure 34:
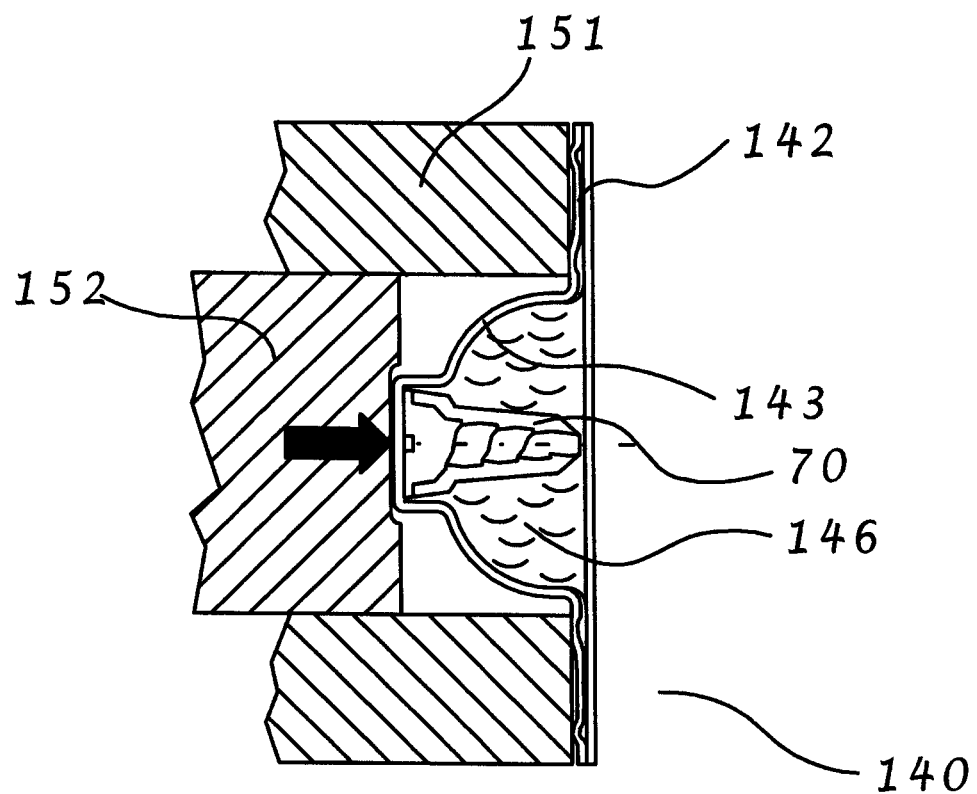
FIG. 34 is a cross section view of a dual medication blister dosage form ready to dispense.

FIG. 33 shows the mixing stage of the device 140. The outer plunger 151 is forced forward compressing the outer chamber 142. The pressure of the liquid in the outer chamber 142 forces the seal 144 between the chambers to release and permits the liquid of chamber 142 to flow into the inner chamber 141 mixing with the first medication. FIG. 34 shows the device when the outer plunger is completely depressed. The outer chamber is completely collapsed and the liquid from that chamber has flowed into the central chamber 141 producing the mixture 145. The skin 143 of the central chamber 141 has popped out to accept the larger volume of the mixture 146. The inner plunger 152 can now be driven into the blister 140 in a manner similar to the devices previously described, thus dispensing the mixed medication through the piercing nozzle 70.

Figure 35:
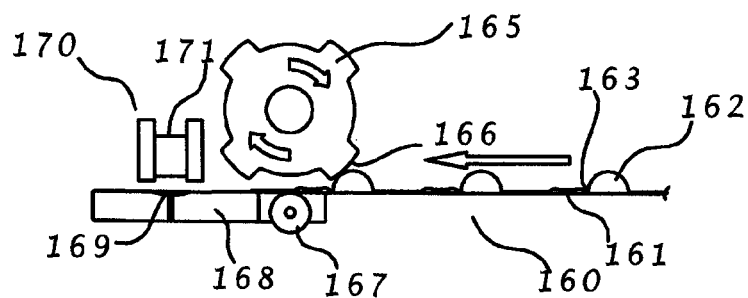
FIGS. 35-38 are schematic view of a strip-type multiple medication dosage form during the steps of moving a dose into position and discharging the dose.

In certain embodiments, mixing of two separate compositions just before dispensing can be accomplished with the device shown in FIG. 35. This example uses a strip of blisters 160 that include an inverted blister 161 containing a first medication and a second blister 162 containing a liquid medication or activating ingredient. The blisters 161 and 162 are joined by a weak adhesive seal 163. The drive wheel 167 is connected to the cog wheel 165 by gears or other structures with similar function such that they turn together and advance the strip 160 between them. The base 168 supports the strip 160 and holds a piercing tip 169 under a plunger mechanism 170.

Figure 36:
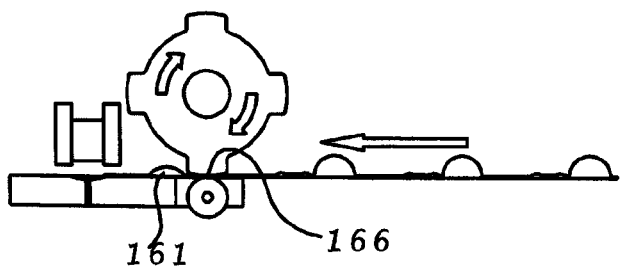
Figure 37:
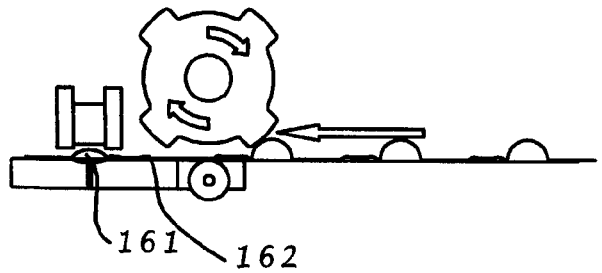

FIG. 36 shows the mechanism in the mixing step. The cog 166 of the cog wheel 165 has crushed the blister 162 containing the second medication or activating ingredient forcing the seal 163 to separate and the second medication or activating ingredient to flow into the first blister 161, popping it up to hold the volume of both blisters. FIG. 37 shows the strip with the mixed medication blister 161 advancing into the dispensing position under the plunger mechanism 170.

Figure 38:
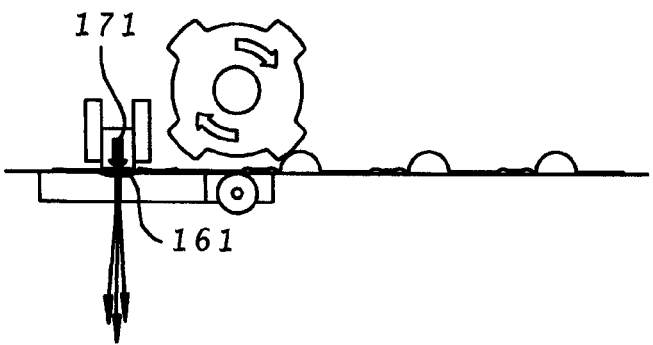

As shown in FIG. 38, the plunger 171 is activated by mechanisms as described herein, collapsing the blister 161 and dispensing the medication. The cog wheel 165 is positioned to compress the next blister 162, thus mixing the medications and move the next mixture under the plunger mechanism 170.

Figure 39:
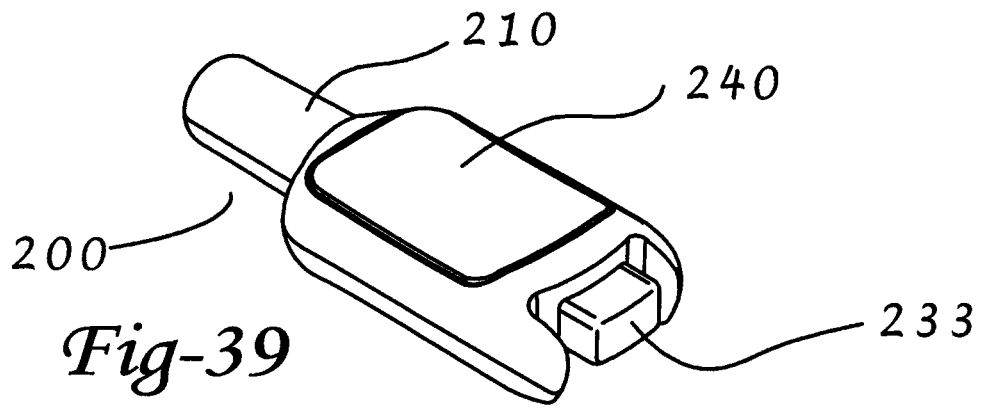
FIG. 39 is a perspective view of a push button delivery device in the storage position.
Figure 40:
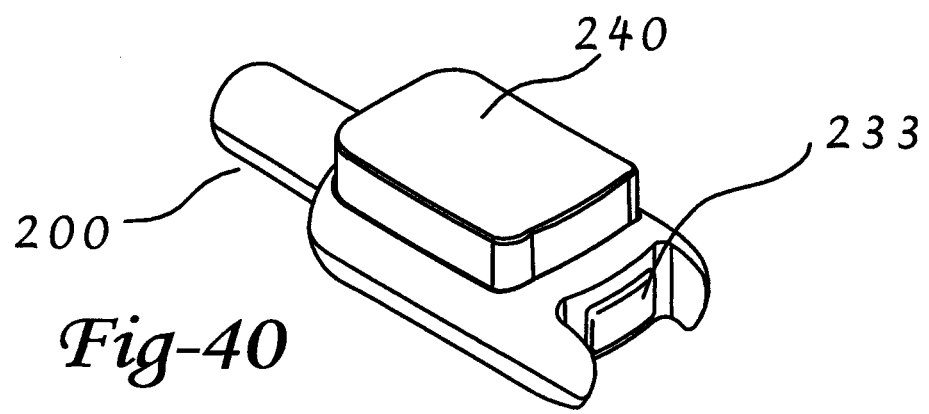
FIG. 40 is a perspective view of a device as shown in FIG. 39 in the ready position.
Figure 41:
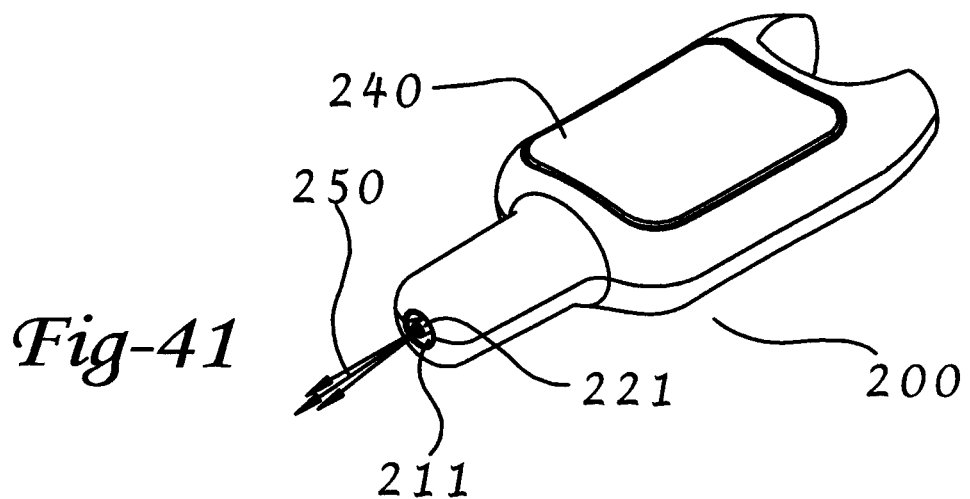
FIG. 41 is a perspective view of a device as shown in FIG. 39 dispensing.

An embodiment of a push-button delivery device is shown in FIG. 39 in the storage position. The delivery device 200 in the storage condition. The device shown includes a body portion 210 configured to deliver a composition to the nasal passage of a user, a push button 240 and an activating pin 233. In the ready position, as shown in FIG. 40, the activating pin 233 has been pressed into the body causing the button 240 to rise into the dispensing position. As shown in FIG. 41, depressing button 240 drives the firing mechanism forcing the piercing nozzle 221 out the dispensing opening 211 and dispensing the medication in a spray pattern 250.

Figure 42:
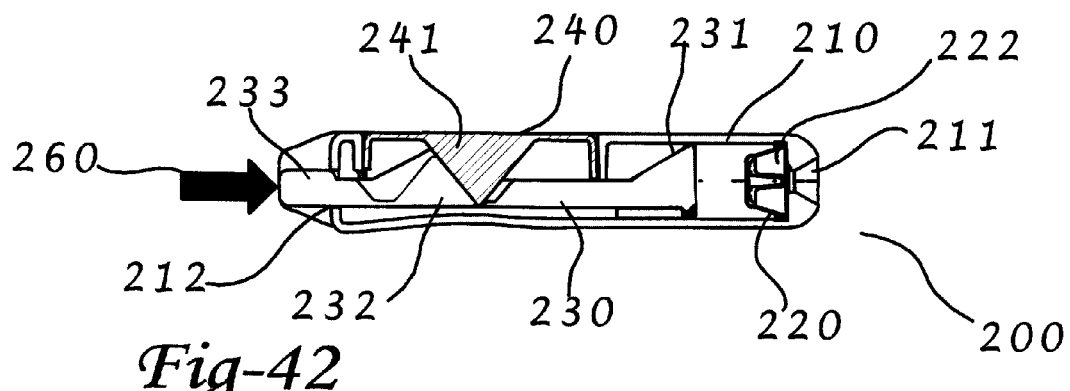
FIG. 42 is a cross-sectional view of a device as shown in FIG. 39 in the storage position.
Figure 43:
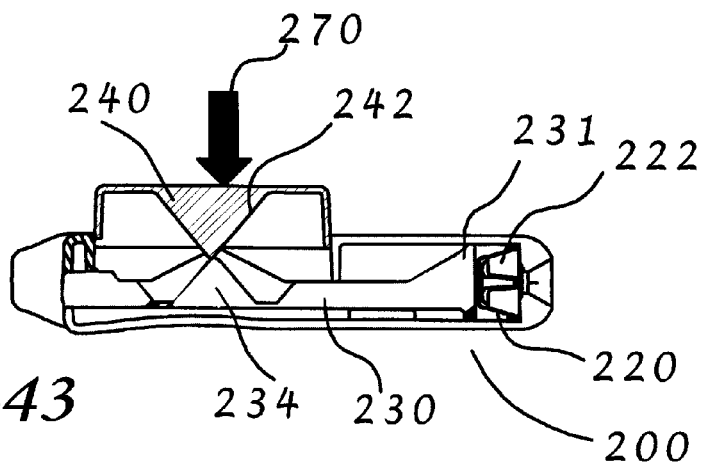
FIG. 43 is a cross-sectional view of a device as shown in FIG. 39 in the ready position.
Figure 44:
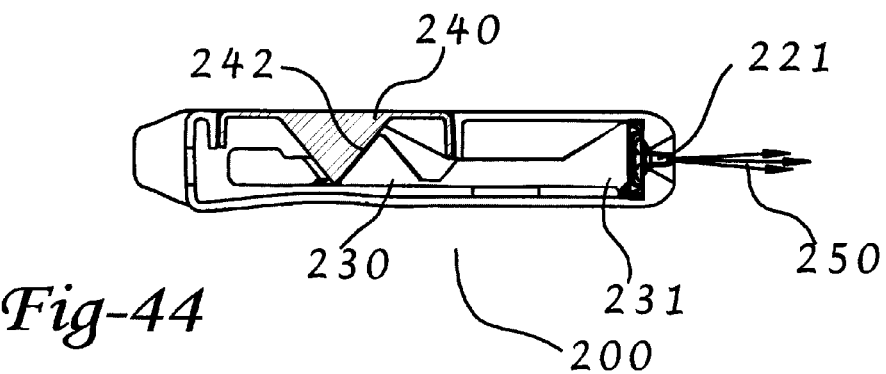
FIG. 44 is a cross-sectional view of a device as shown in FIG. 39 dispensing.

The operation of the device can be better understood by referring to the cross sectional drawings, FIGS. 42-44. In the storage condition (FIG. 42) the main slide or ram 230 is positioned in the body 210 such that the activating pin 233 extends out the rear opening 212 of the body and the angled surface cam 232 of the main slide 230 is positioned adjacent a matching angle cam 241 on the underside of the button 240. When a first force in the direction shown by the arrow 260 is applied to the activating pin 233, it causes the main slide 230 to move forward and raise the button 240 up into the ready position (FIG. 43). This motion of the main slide 230 positions the plunger end 231 adjacent to the dosage blister 220 and positions the slide angle surface 234 in alignment with button angle surface 242 of the button 240. Applying a second force in the direction shown by the arrow 270 to the button 240 forces the main slide 230 forward, crushing the dosage form 220 and discharging the medication 222 out the piercing nozzle 221 in a spray pattern 250 (FIG. 44). The interaction of the two inclined surfaces of the main slide cam and the button angled cam as the slide is moved forward raises the button angled cam surface to the apex of the slide angled cam, consequently pushing the firing button up into the ready position. The apex of the slide angled cam moves slightly past the apex of the button angled cam so the rearward facing surface of the slide angled cam is in contact with the forward facing surface of the button angled cam.

Figure 45:
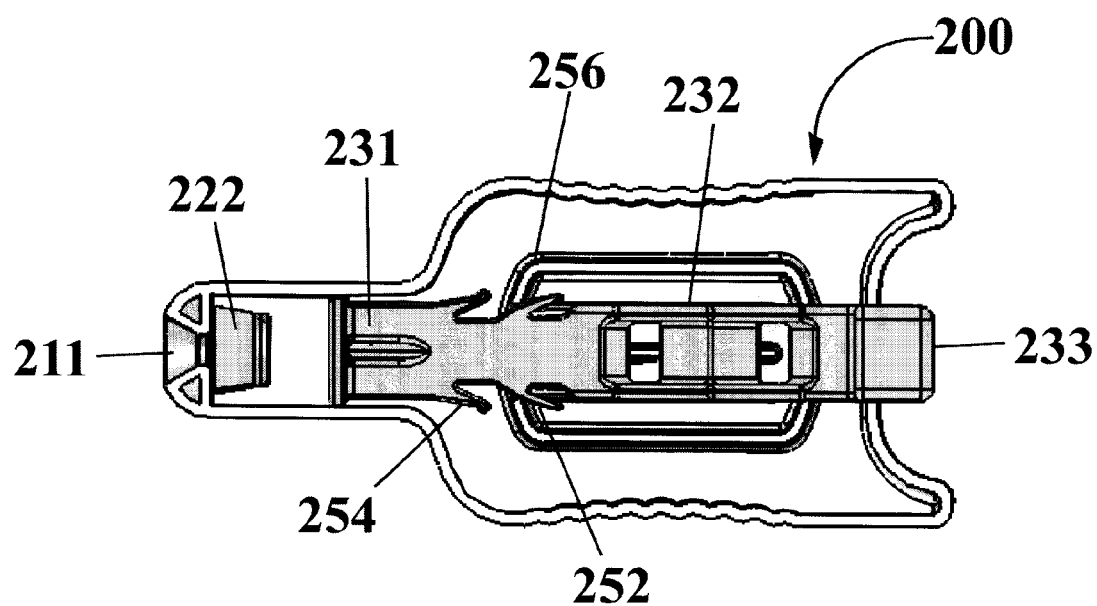
FIG. 45 is an embodiment of the device with a push button mechanism in the storage position with the upper half of the body removed.
Figure 46:
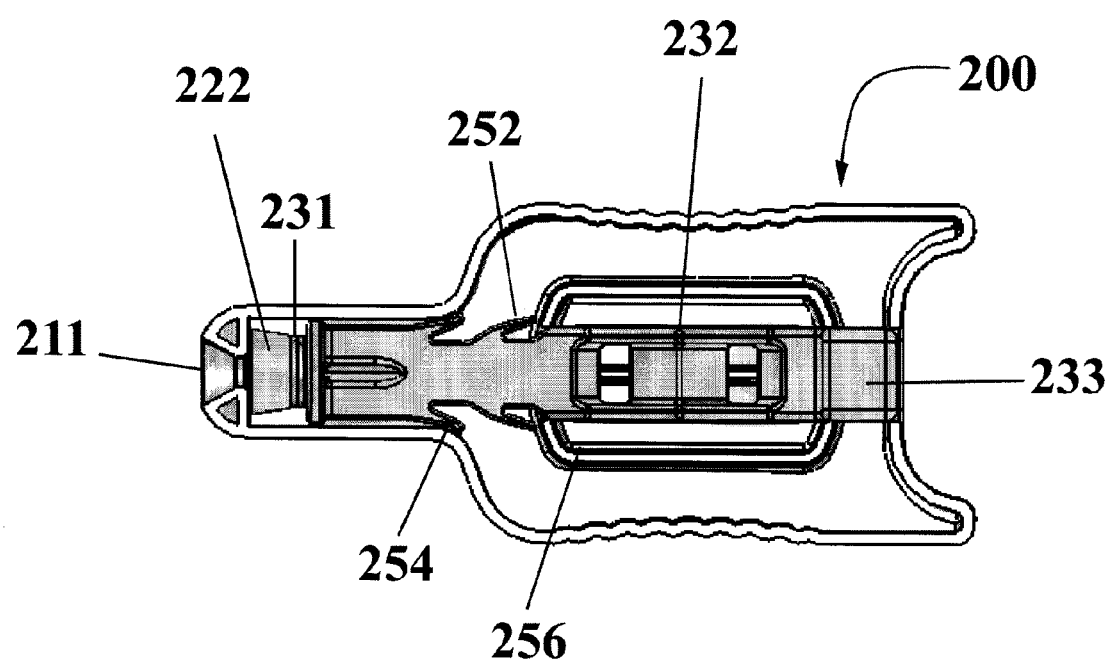
FIG. 46 is the device as shown in FIG. 45 in the ready position.

Further features of the devices can be seen in FIGS. 45 and 46, which depict a push button device with the upper half of the body removed. The device shown in FIG. 45 is in the storage position. The activation pin 233 is "out" and the slide angled surface cam 232 is near the back of the device, or the end furthest from the spray nozzle 211. A first set of detents 252 are impeded by a ridge 256, and the plunger end 231 is spaced apart from the dosage form 222. The detents 252 produce an auditory snap when the device is placed in ready position.

The device as shown in FIG. 45 is in the ready position. As can be seen, the first set of detents 252 have released and moved past the ridge 256. A second set of detents 254 is now held against the body, inhibiting further motion of the slide, and assuring that sufficient force must be applied to the firing button to release the detents and crush the dosage form with sufficient force to create the desired spray pattern.

With the device is in the ready position, the firing button is pressed until the second detents are overcome, and the button angled cam is forced down on the slide angled cam. Because of the interaction of the inclined planes, the slide is forced forward with a mechanical advantage relative to the force applied to the button, driving the plunger end 231 into the dosage form 222 with sufficient force to crush the dosage form and expel the liquid contents in the desired spray pattern (FIG. 46).

Figure 47:
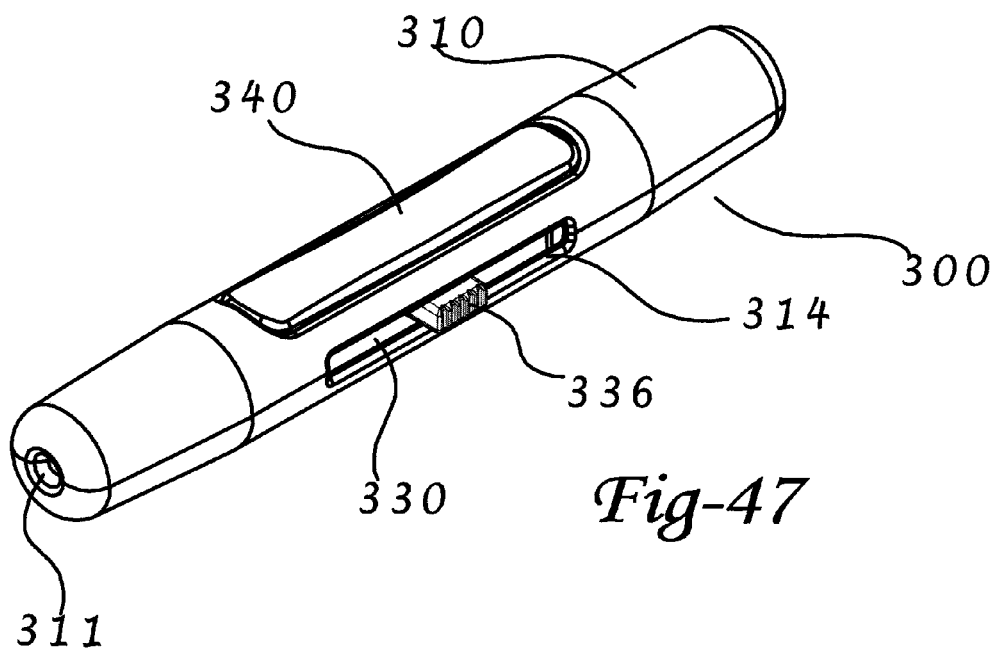
FIG. 47 is a perspective view of a dual delivery device in the storage position.
Figure 48:
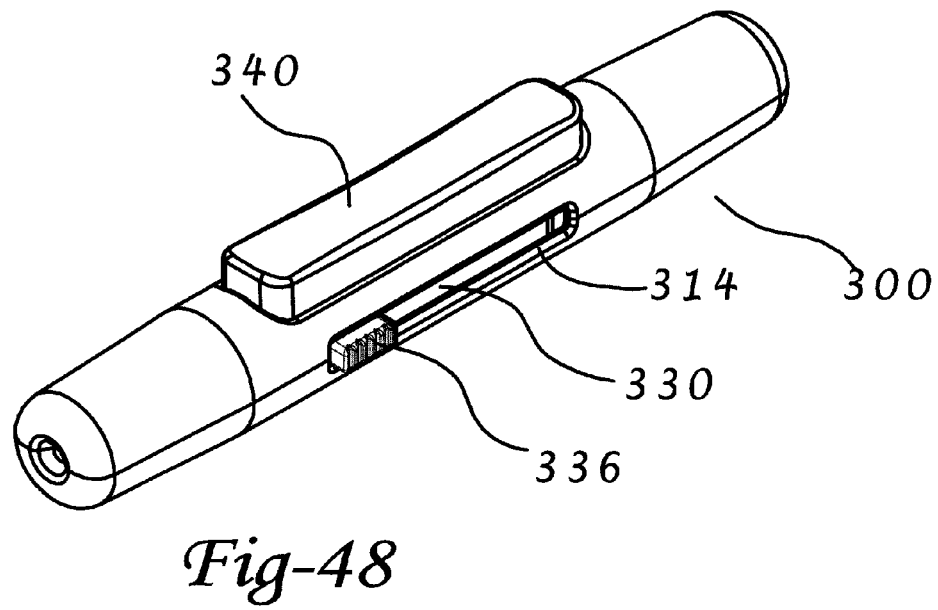
FIG. 48 is a perspective view of the device of FIG. 47 in the ready position.
Figure 49:
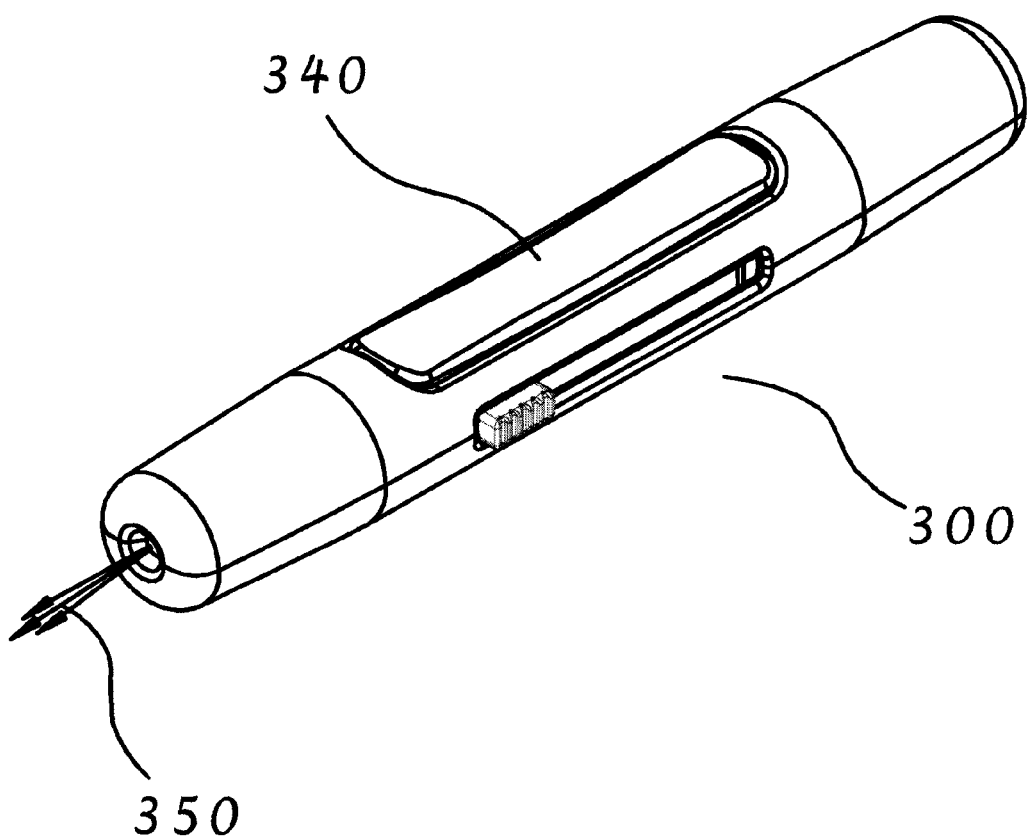
FIG. 49 is a perspective view of the device of FIG. 47 dispensing.
Figure 50:
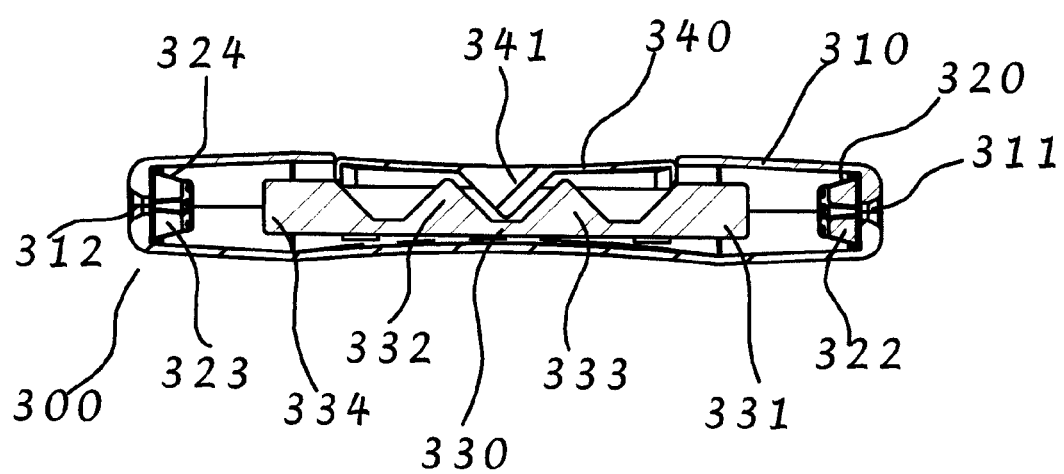
FIG. 50 is a cross-sectional view of a device as shown in FIG. 47 in the storage position.

An embodiment of a delivery device 300 for dispensing dual dosages is shown in the storage condition in FIG. 47. The device includes a main slide 330 with an activating tab 336 extending through opening 314. The main slide 330 is contained in the body 310, which has a first outlet opening 311 on one end and a second outlet opening 312 on the opposing end. The device also includes a firing button 340. As shown in FIG. 48, sliding the activating tab 336 toward the first outlet opening 311 raises the button 340 into the ready position. Depressing button 340 fires the device, and dispenses the contents through the first outlet opening 311 in the desired spray pattern 350 as shown in FIG. 49.

The operation of the device can be better understood by referring to the cross section drawings in FIGS. 50-54. In the storage condition the main slide 330 is located in a neutral position with first angle cam 332 and second angled cam 333 on opposite sides of button angled cam 341. The main slide also has a first plunger end 331 on one end and a second plunger end 334 on the opposite end. Body 310 also contains first dosage form 320 adjacent to first discharge opening 311 and second dosage form adjacent to second discharge opening 312.

Figure 51:
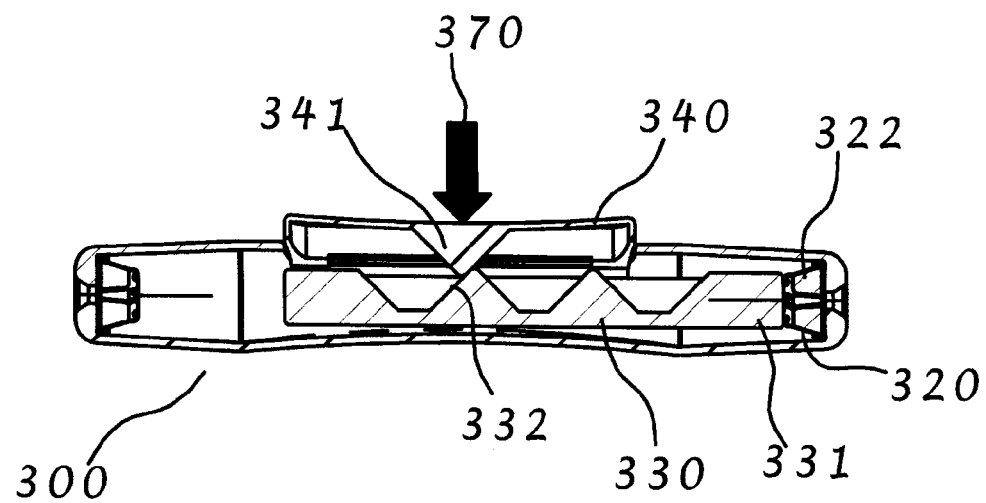
FIG. 51 is a cross-sectional view of a device as shown in FIG. 47 in the ready position for a first delivery.
Figure 52:
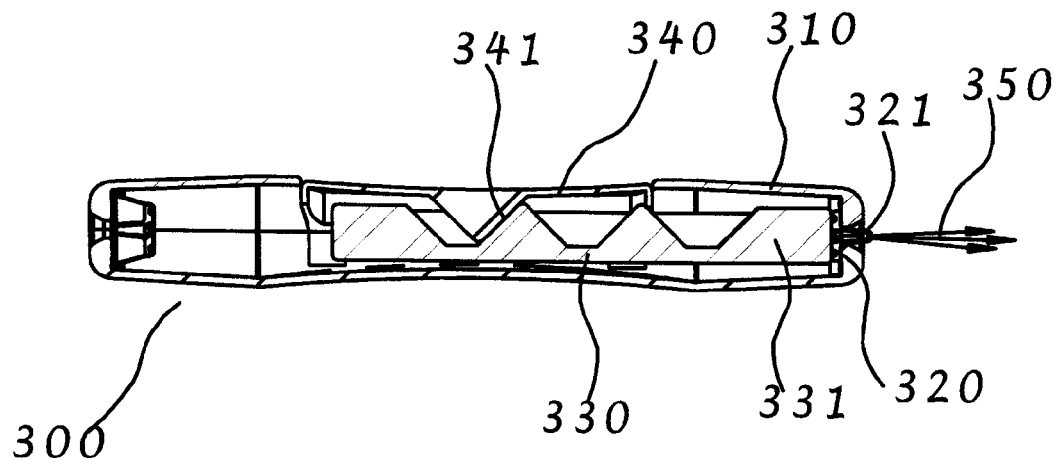
FIG. 52 is a cross-sectional view of a device as shown in FIG. 47 dispensing the first delivery.

Sliding the activating tab 336 toward the first end of the body 310, as shown in FIG. 51, positions the first plunger end 331 against the first dosage form 320, raises the button 340 and positions the first angle cam 332 in alignment with button angle cam 341. When a force is applied in the direction indicated by arrow 370 to the button 340, the main slide 330 is driven into the first dosage form 320, crushing it and discharging medication 322 out piercing nozzle 321 in spray pattern 350 (FIG. 52).

Figure 53:
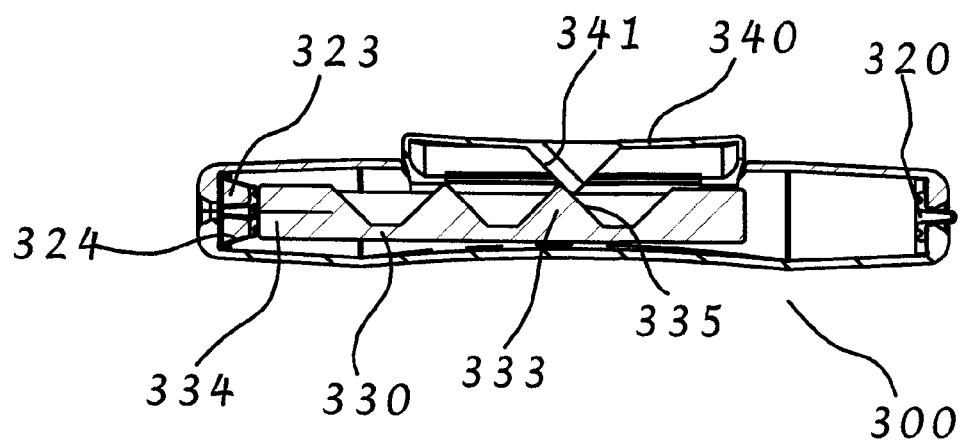
FIG. 53 is a cross-sectional view of a device as shown in FIG. 47 in the ready position for the second delivery.
Figure 54:
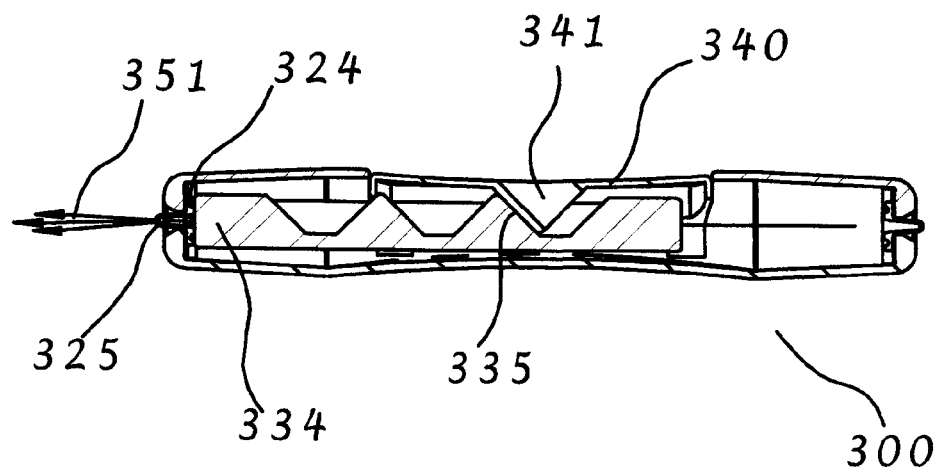
FIG. 54 is a cross-sectional view of a device as shown in FIG. 47 dispensing the second delivery.

To dispense the second dose of medication, the activating tab 336 is moved in the reverse direction to the position shown in FIG. 53, positioning the second plunger end 334 against the second dosage form 324, raising the button 340 and positioning the second angle cam 333 in alignment with button angle cam 341. In similar manner (FIG. 54), depressing button 340 drives the main slide 330 in the opposite direction, crushing second dosage form 324 and discharging medication 323 through piercing nozzle 325 in spray pattern 351.

Figure 55:
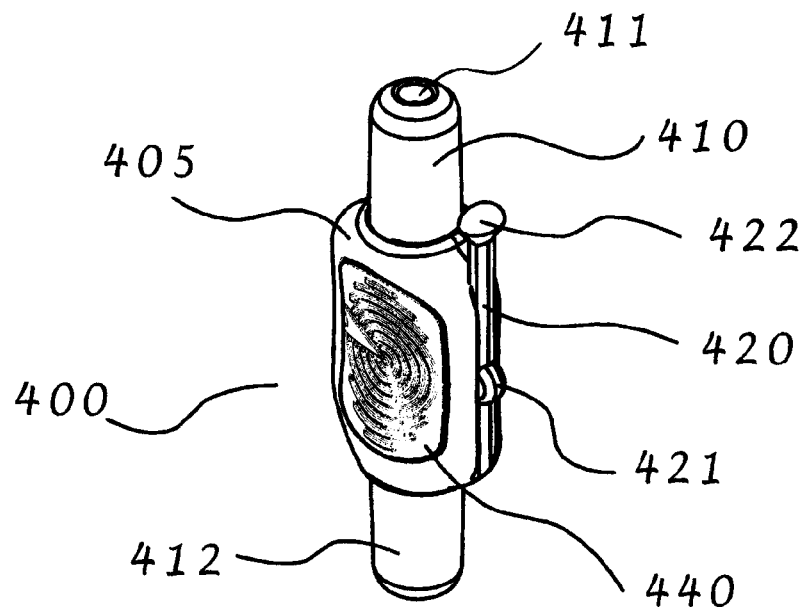
FIG. 55 is a device for dispensing two separate doses from opposing ends of the device.
Figure 56:
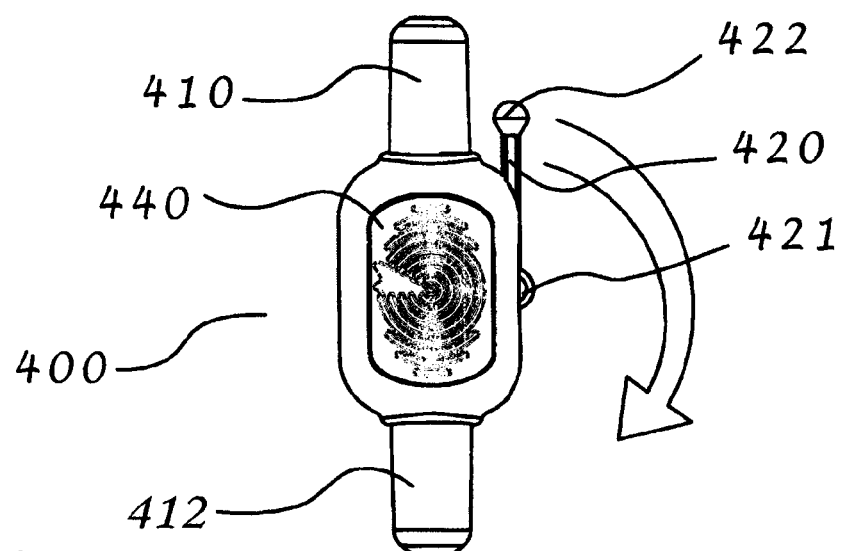
FIG. 56 shows the operation of a lever on the device shown in FIG. 55 for placing the device in ready position to dispense the first dose.
Figure 57:
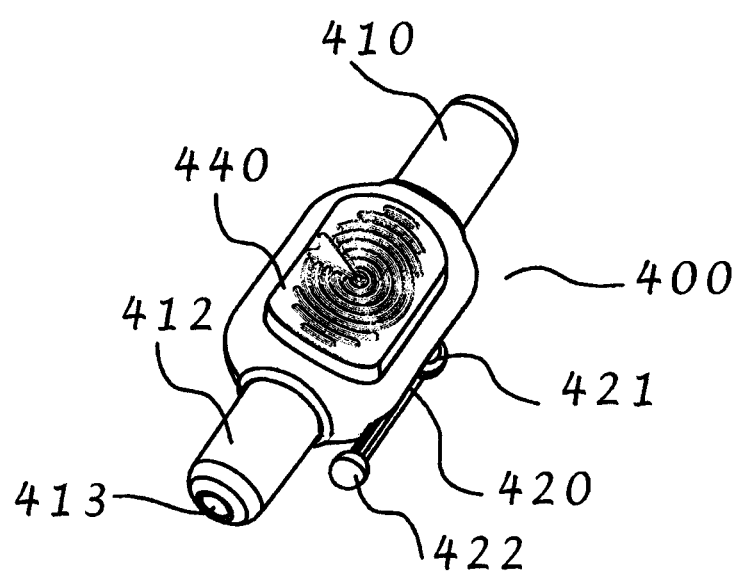
FIG. 57 shows the device of FIG. 55 in ready position for the first dose.

An additional device for dispensing two medications or the same medication in two doses is shown in FIG. 55. The device 400 includes body 405 and a first dispensing chamber 410 with discharge nozzle 411 shaped and sized to deliver a dose into a human nostril. The device also includes an oppositely disposed second dispensing chamber 412 with second discharge nozzle 413 (FIG. 57) also shaped and sized to deliver a dose into a human nostril from the opposite end of the device. The device 400 includes a mechanism to place the device in ready mode and a firing system. Although various firing mechanisms as shown in herein can be used in the device, a preferred mechanism is a double inclined plane mechanism similar to that shown in FIGS. 42 through 46. The device in FIG. 55 is shown in a storage position. A lever 420 mounted on one side of the device is used to place the device in ready position for firing a dose of medication through the first nozzle. The lever 420 mounted on one side of body 405 rotates around pivot point 421. A knob 422 is also provided to aid a user in operating the lever. Rotation of the lever 420 around pivot point 421 away from the first dispensing chamber 410 as shown in FIG. 56, moves the internal mechanism, resulting in raising the button 440 to the ready position and placing a ram adjacent a dosage form in the first dispensing chamber 410. Depressing the button 440 then dispenses the medication from first dispensing chamber 410. Rotating lever 420 back to the original position re-raises button 440 to the ready position in preparation for dispensing the medication contained in the second dispensing chamber 412. When the device is in the ready position to dispense from the second nozzle, the lever 420 and knob 422 are positioned near the first nozzle, in a position to interfere with an attempt to insert the first dispensing chamber into a nostril. This provides a measure of safety against inserting the spent dispensing chamber into the nostril and firing a dose from the other end.

Figure 58:
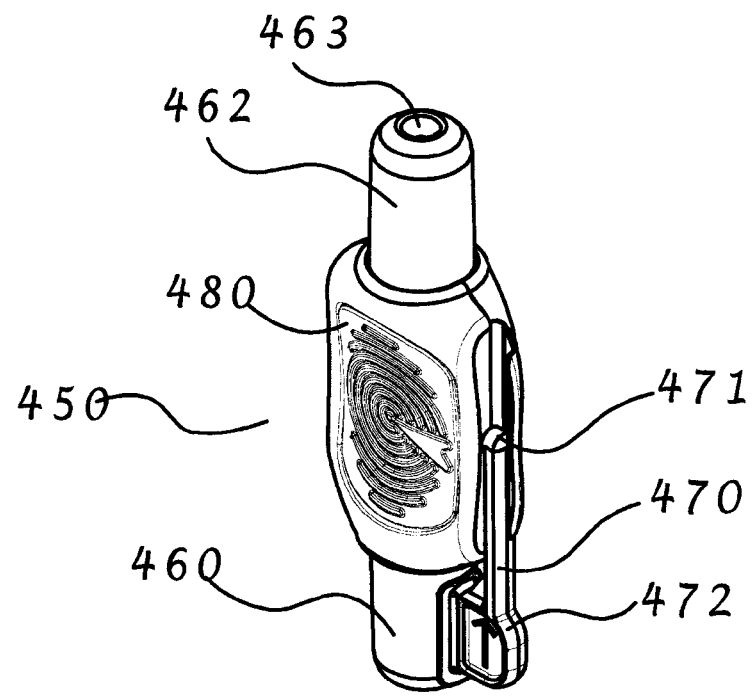
FIG. 58 is an alternative configuration for a device for dispensing two separate doses from opposing ends of the device.
Figure 59:
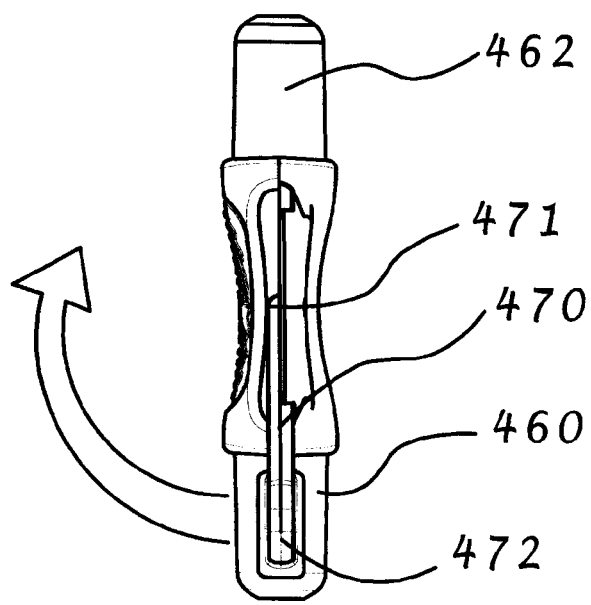
FIG. 59 shows the operation of the lever of the device shown in FIG. 58 to place the device in ready position to dispense the first dose.
Figure 60:
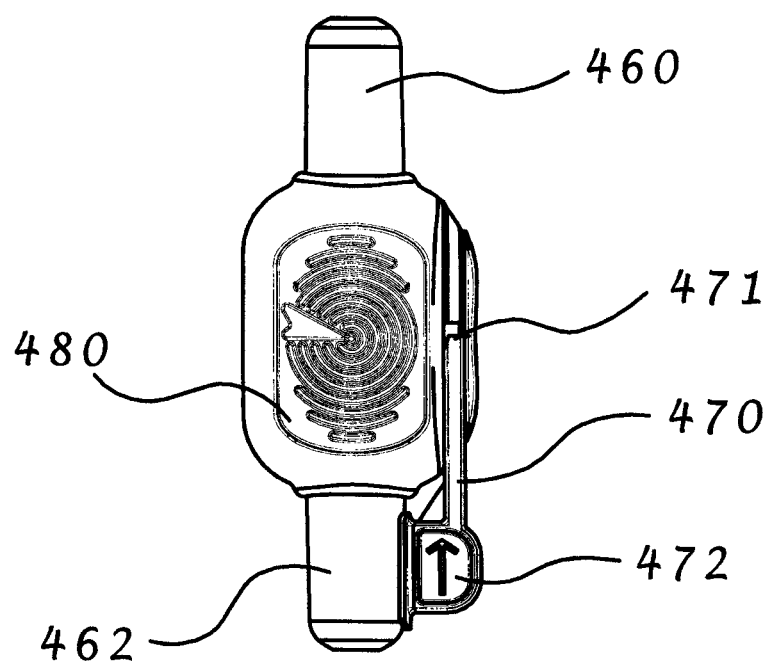
FIG. 60 shows the device of FIG. 58 in ready position to dispense the first dose.

An alternative to the previous device is shown in FIG. 58. The device 450, also includes a first and second dispensing chambers 462, 460, and nozzles 463, disposed at either end of the device. A lever 470 is rotated around pivot point 471 in a plane perpendicular to the rotation of the lever in device 400 as shown by the arrow in FIG. 59. Rotation of the lever 470 again causes the internal mechanism to activate the button 480, raising it to the ready position as shown in FIG. 60. The activated device has the button 480 raised and ready to dispense the medication from first dispensing chamber 460. As can be seen in the drawing, the knob 472 is contact with the second dispensing chamber 462, preventing the insertion of the incorrect chamber into the nostril. The knob can also include an indicator such as the arrow shown, reminding the user of the direction for dispensing the dosage. After dispensing the medication contained in first dispensing chamber 460, lever 470 is rotated back to the original position, activating the device to dispense the medication from second dispensing chamber 462 and blocking insertion of the dispensing chamber 460 into the nostril.

There are occasions when it is desirable to introduce medication to both sides of the nose or nostrils. It may be preferred to introduce the medication or medications simultaneously or sequentially. Additionally, each nostril may receive the same medication, or a different medication may be delivered to each side.

Figure 61:
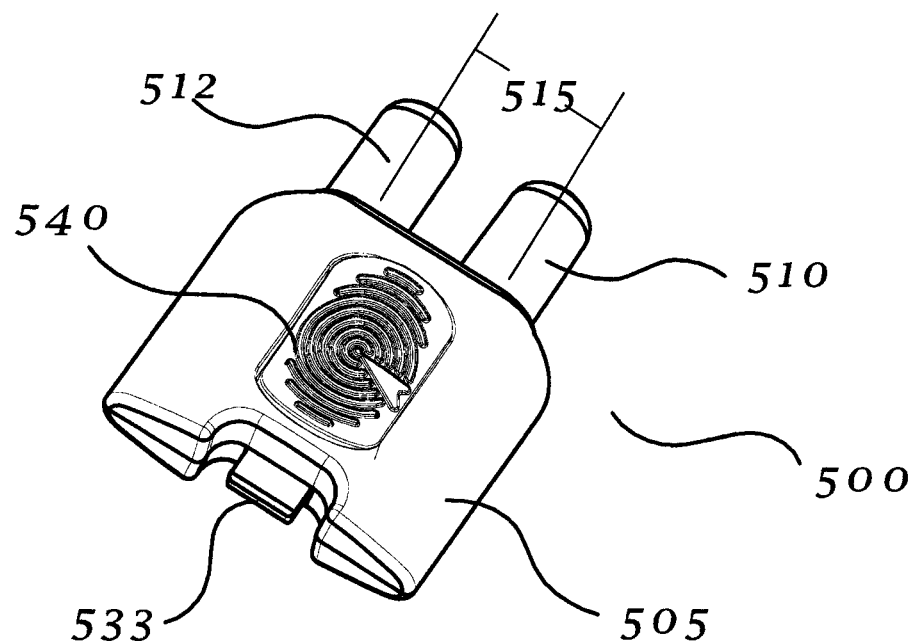
FIG. 61 is a device for dispensing two doses in side-by-side arrangement.
Figure 62:
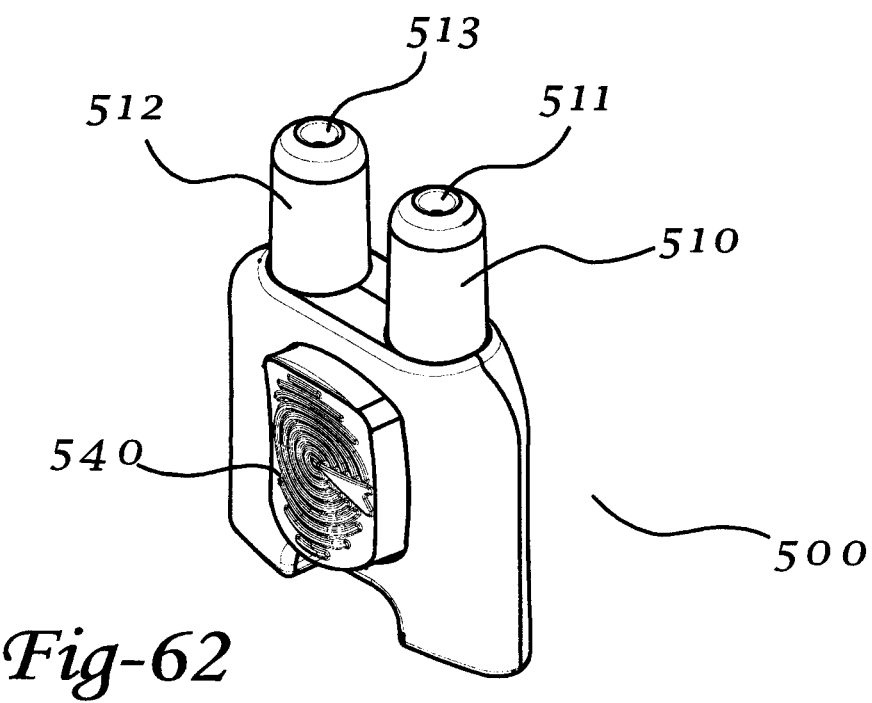
FIG. 62 shows the device of FIG. 61 in the ready position with the firing button in raised position.

A device for administration of two dosages in a side-by-side arrangement is shown in FIGS. 61 and 62. The device 500 includes a body 505 and two outlet chambers, right chamber 510 and left chamber 512 located side by side and parallel, separated by distance 515 so that they fit simultaneously into both nostrils of an average adult user. It is understood that devices can also be produced in various sizes to fit the needs of users, including even a smaller size for use by children. The device can include any appropriate internal mechanism as described herein in relation to the other devices, the device shown can include a double inclined plane mechanism as shown in the single dosage version in FIGS. 39 through 44. Pressing the activating pin 533 raises the button 540 and prepares both dispensing chambers 510 and 512 to be discharged as shown in FIG. 62. In one embodiment, depressing the button 540 discharges both chambers simultaneously. In a second embodiment of the device, depressing button 540 discharges the medication in one chamber 510, through discharge nozzle 511 and forces the activating pin 533 back to its original position. The second pressing of the activating pin 533 raises button 540 and prepares the second chamber 512 to be discharged by depressing the button 540 again. Thus each outlet chamber 510 and 512 may contain the same or different medication and may be administered together or sequentially.

Figure 63:
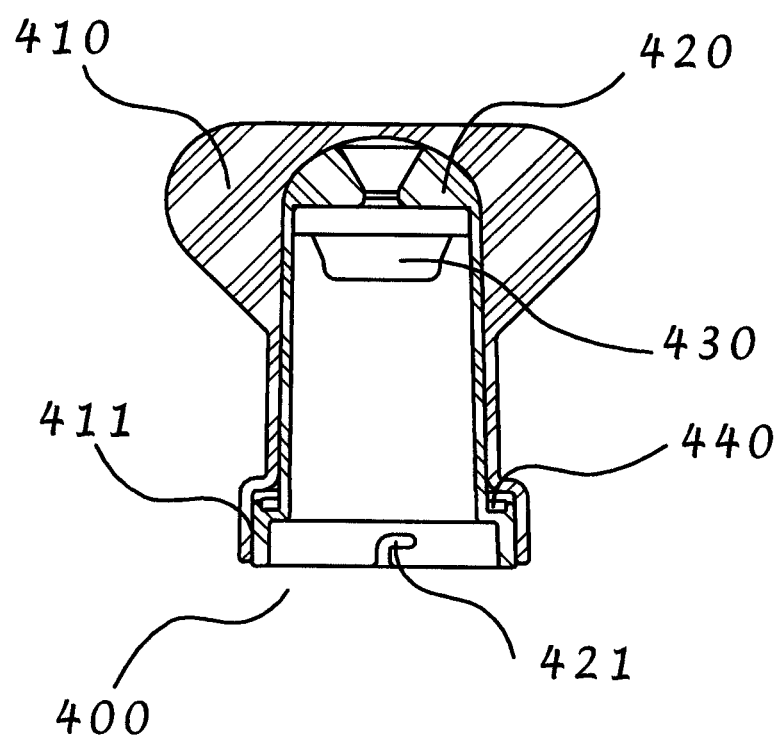
FIG. 63 is a cross section of a marking tip assembly.
Figure 64:
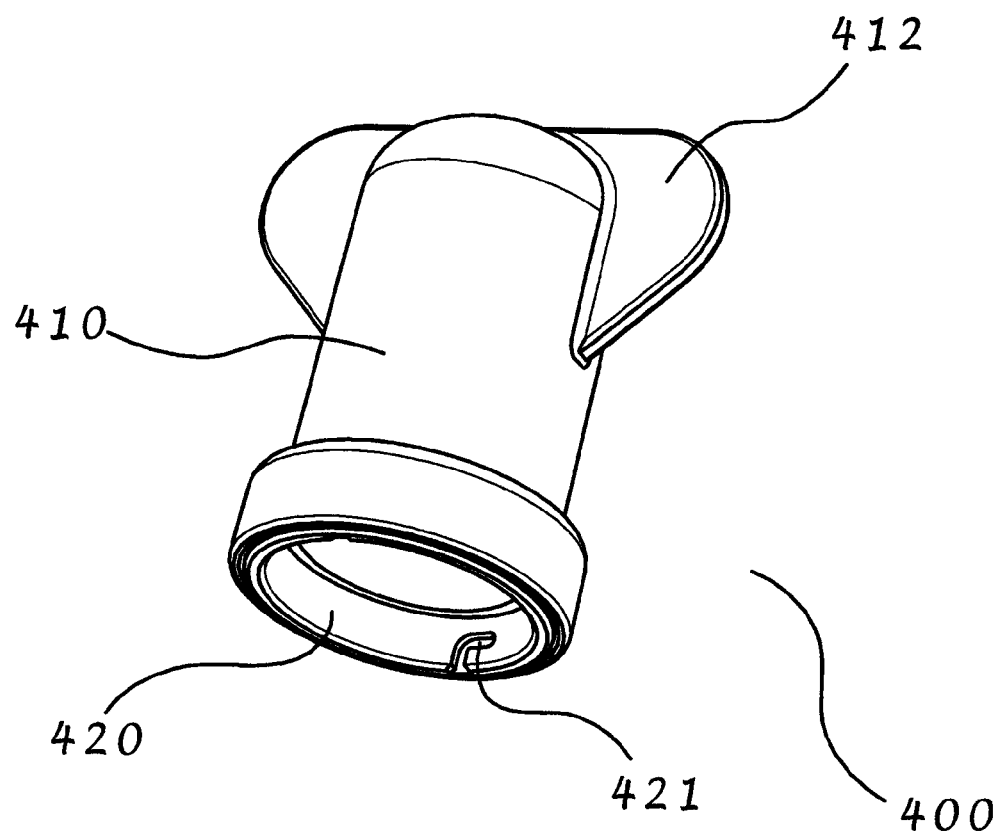
FIG. 64 is a perspective view of a marking tip assembly.

A preferred embodiment of a marking tip assembly 600 is shown in cross-section in FIG. 63. The assembly shown in the Figure is designed to be used as a disposable tip containing a dosage form. The disposable tip can be used on dispensing devices such as those shown in FIGS. 31 and 32 and similar devices. The assembly includes a cap 610, a dispensing tip 620, a dosage form 630 and an ink pad 640. The cap 610 forms a seal against the dispensing tip 620 along area 611 preventing the ink from drying prior to use. The dispensing tip 620 contains bayonet receptacles 621 for mating to a dispensing device 650 (shown in FIG. 65). The marking tip assembly of FIG. 63 is shown in perspective view in FIG. 64. In this view, the ears 612 are more clearly seen. These ears are useful for twisting the assembly in order to engage the bayonet receptacles 621 with the tabs 652.

Figure 65:
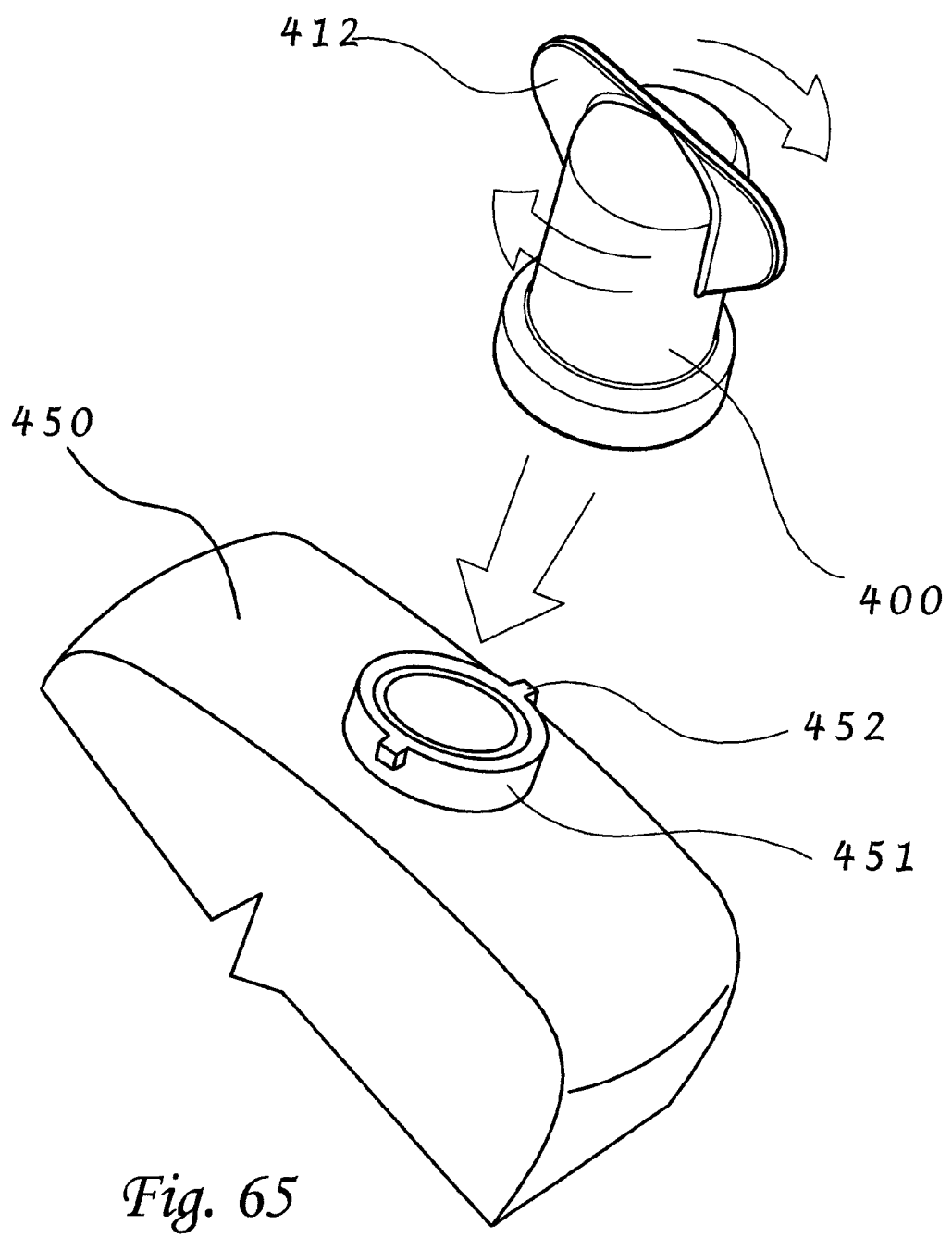
FIG. 65 is a marking tip assembly ready to be installed on a dispensing device.

FIG. 65 illustrates how the marking tip assembly 600 is installed on a dispensing device 650. The marking tip assembly 600 is placed on a protrusion 651 on the dispensing device 650 with bayonet receptacles aligned with tabs 652. When properly aligned the assembly is pressed down and twisted as shown by the arrows. The twist first locks the tip 620 to the dispensing device 650 and a further twist releases the cap 610 from the tip 620.

Figure 66:
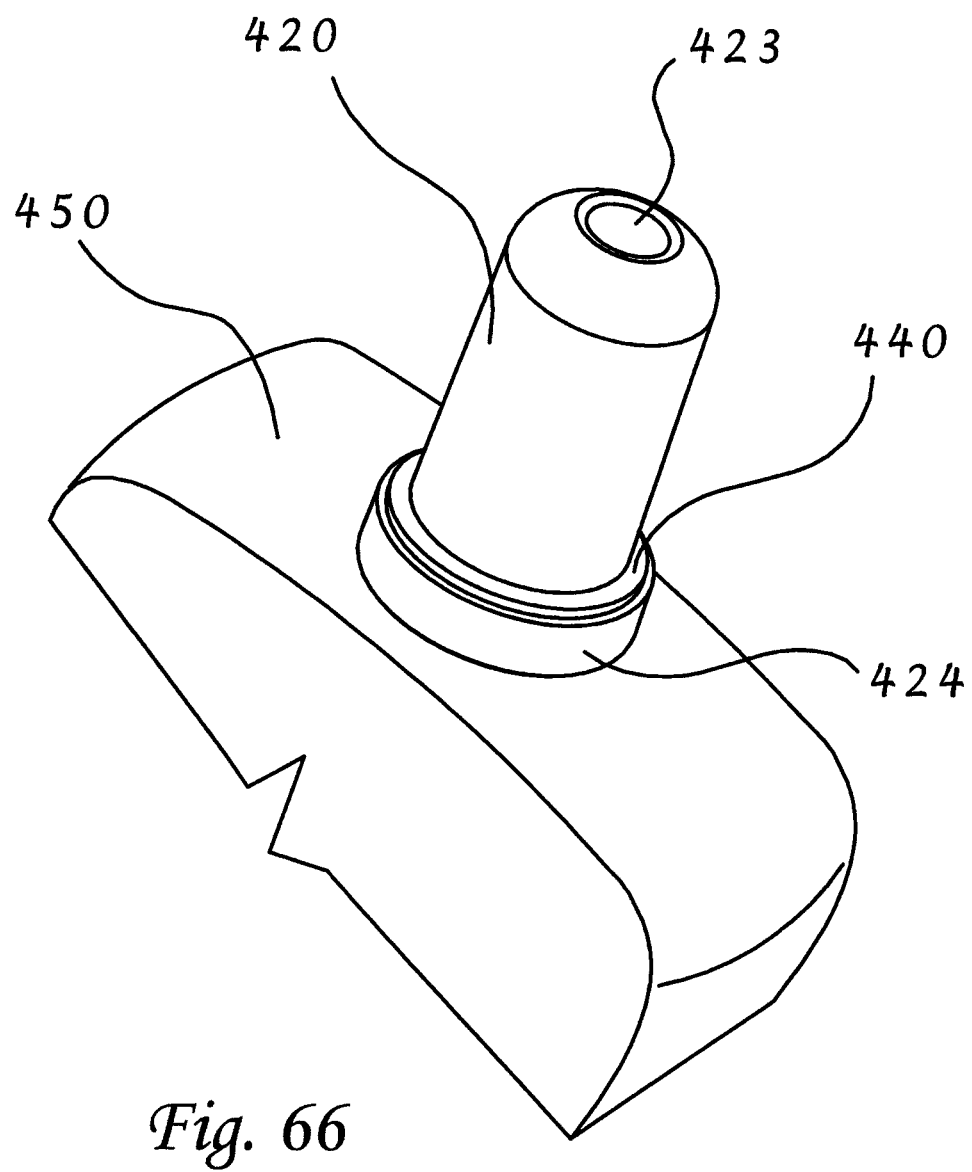
FIG. 66 is a marking tip assembly ready to dispense with a tip in place a dispensing device.

FIG. 66 shows the device ready to dispense with tip 620 in place on the dispensing device 650 and the cap removed. When the cap 610 is removed from the tip 620, the discharge opening 623 and the ink pad 640 are exposed. When the tip 620 is inserted into the patient's nostril, the ink pad 640 makes contact with the external rim of the nostril, leaving a mark.

All of the devices and methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the methods described herein without departing from the concept, spirit and scope of the invention. All such similar substitutes and modifications apparent to those skilled in the art are deemed to be within the spirit, scope and concept of the invention as defined by the appended claims.

The invention claimed is:

1. A device for dispensing a predetermined quantity of sterile fluid, said device comprising:
   a body, and a dispensing mechanism, the dispensing mechanism comprising:
   a firing button comprising an inclined surface;
   a sliding member contained within the body and comprising one or more angled cam surfaces and wherein one of said angled cam members contacts said inclined surface of the firing button;
   a plunger end connected to the sliding member; and
   a chamber containing a crushable blister, said crushable blister comprising a piercable membrane and an internal volume, wherein said internal volume contains a piercing mechanism comprising an elongated member with one or more inlets in fluid communication with the internal volume, an internal channel and a piercing end, forming a discharge nozzle;
   wherein, forcing the firing button against the cam forces the plunger end into the dispensing chamber with a mechanical advantage relative to the force applied to the firing button, crushing the blister against the piercing mechanism and dispensing the contents of the blister through the nozzle.

2. The device of claim 1, wherein the sterile fluid comprises a liquid.

3. The device of claim 1, wherein the sterile fluid comprises a powder.

4. The device of claim 1, wherein the piercing mechanism comprises:
   an internal channel;
   one or more inlet openings arranged to force one or more bends as the fluid flows into the internal channel;
   a discharge outlet; and
   features in the internal channel to control the spray pattern and droplet size of a fluid forced to flow through the nozzle.

5. The device of claim 4, wherein the features in the internal channel of the piercing mechanism comprise steps, flutes, ribs, or a combination thereof.

* * * * *